US011510605B2

(12) United States Patent
Eguchi et al.

(10) Patent No.: US 11,510,605 B2
(45) Date of Patent: Nov. 29, 2022

(54) INSTANTANEOUS HEARTBEAT RELIABILITY EVALUATION DEVICE, METHOD, AND PROGRAM

(71) Applicant: Nippon Telegraph and Telephone Corporation, Tokyo (JP)

(72) Inventors: Kana Eguchi, Tokyo (JP); Ryosuke Aoki, Tokyo (JP); Kazuhiro Yoshida, Tokyo (JP); Tomohiro Yamada, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 55 days.

(21) Appl. No.: 17/056,269

(22) PCT Filed: May 22, 2019

(86) PCT No.: PCT/JP2019/020321
§ 371 (c)(1),
(2) Date: Nov. 17, 2020

(87) PCT Pub. No.: WO2019/225662
PCT Pub. Date: Nov. 28, 2019

(65) Prior Publication Data
US 2021/0244338 A1  Aug. 12, 2021

(30) Foreign Application Priority Data

May 24, 2018 (JP) .............................. JP2018-099962

(51) Int. Cl.
*A61B 5/00* (2006.01)
*A61B 5/352* (2021.01)
*A61B 5/333* (2021.01)

(52) U.S. Cl.
CPC .............. *A61B 5/352* (2021.01); *A61B 5/333* (2021.01)

(58) Field of Classification Search
CPC ..... A61B 5/325; A61B 5/024; A61B 5/02405; A61B 5/366; A61B 5/35;
(Continued)

(56) References Cited

U.S. PATENT DOCUMENTS 4,589,420 A * 5/1986 Adams ................. A61B 5/7264
600/515

OTHER PUBLICATIONS

Eguchi et al., "Detection Method of Noise Contamination Region for Wearable Electrocardioraph-Non-Filterable Noise Detection Method for Wearable ECG Devices," IEICE Technical Report, 2015, 115(345):27-32, 19 pages (with English Translation).
(Continued)

*Primary Examiner* — Scott M. Getzow
(74) *Attorney, Agent, or Firm* — Fish & Richardson P.C.

(57) ABSTRACT

An instantaneous heartbeat reliability evaluation apparatus includes: extraction means which extracts waveforms having a maximum value corresponding to depolarization of a heart in a biosignal of an examinee; first calculation means which calculates an interval between two waveforms neighboring in a time series; dividing means which divides a signal output from measurement means into signals of predetermined periods; second calculation means which calculates feature quantities of a potential of each divided signal; first evaluation means which evaluates whether a measurement state of each divided signal is normal or abnormal on the basis of feature quantities; and second evaluation means which evaluates measurement states of two neighboring extracted waveforms on the basis of an evaluation result obtained by the first evaluation means and evaluates reliability of a measurement state of the interval between the waveforms depending on a type of the evaluated measurement states of the waveforms.

15 Claims, 10 Drawing Sheets

(58) Field of Classification Search
CPC ............ A61B 5/72–7221; A61B 5/333; A61B 5/0245; A61B 5/7217
See application file for complete search history.

(56) References Cited

OTHER PUBLICATIONS

Eguchi et al., "Evaluation of RRI Measurement Reliability for Wearable Electrocardiograph Using QRS Group Potential Characteristics—Reliability Evaluation of R-R Interval Measurement Status using the Electric Potential Characteristics of QRS Complex for Wearable ECG Devices," IEICE Technical Report, 2017, 116(412):171-176, 13 pages (with Machine Translation).

Sakuma et al., "A Real-Time Relaxation System at Sitting Position using Heart Rate Measurement," Multimedia, Distributed, Collaborative and Mobile Symposium, Jul. 2013, 2013(2):1188-1195, 17 pages (with English Translation).

Yakota et al., "Prodromal Monitoring of Sepsis Using Heart Rate Variability Over Time—Monitoring of Sepsis Premonitories Using Time Series of Heart Rate Variability," The Japan Society of Mechanical Engineers, Presented at the 54 Automatic Control Alliance Lecture Meeting, Nov. 19, 2011, pp. 1258-1261, 9 pages (with English Translation).

* cited by examiner

INSTANTANEOUS HEARTBEAT RELIABILITY EVALUATION DEVICE, METHOD, AND PROGRAM

CROSS-REFERENCE TO RELATED APPLICATIONS

This application is a National Stage application under 35 U.S.C. § 371 of International Application No. PCT/JP2019/020321, having an International Filing Date of May 22, 2019, which claims priority to Japanese Application Serial No. 2018-099962, filed on May 24, 2018. The disclosure of the prior application is considered part of the disclosure of this application, and is incorporated in its entirety into this application.

TECHNICAL FIELD

Embodiments of the present invention relate to an instantaneous heartbeat reliability evaluation apparatus, method, and a program.

BACKGROUND ART

Autonomic nerves are divided into two types of nerves, sympathetic nerves and vagus nerves. The sympathetic nerves and the vagus nerves are widely distributed in organs and the like and control involuntary physical functions including circulation and metabolism. In many cases, it is said that the sympathetic nerves and the vagus nerves antagonistically control one organ.

It is known that sympathetic neural activity that is a kind of autonomic neural activity is exacerbated by stress stimuli such as a mental arithmetic load.

Meanwhile, vagus neural activity that is another kind of autonomic neural activity is understood as the same as parasympathetic neural activity in many cases because the vagus nerve mainly takes charge of parasympathetic neural activity in each organ.

In a strict sense, the vagus nerve is the name of the tenth cranial nerve and includes all nerves extending from the brain to organs.

Accordingly, there are cases in which parasympathetic neural activity in an organ that is a control target is indicated by adding the name of the target organ, such as a heart vagus nerve, for example.

The heart may be mentioned as an example of an organ controlled by autonomic nerves. The heart is antagonistically controlled by the sympathetic nerve and the vagus nerve and is said to reflect a static balance between sympathetic neural activity and vagus neural activity.

FIG. 9 is a diagram showing an example of instantaneous heartbeat (RRI: R-R interval). It is known that variation in the instantaneous heartbeat that is an interval between two neighboring R waves in a time series (hereinafter simply referred to as "neighboring" in some cases) as shown in FIG. 9 changes according to both the sympathetic neural activity and the vagus neural activity.

Meanwhile, an R wave is a kind of electrocardiographic waveform obtained through electrocardiogram (ECG) measurement and reflects the depolarization activity of the heart.

As a method of estimating autonomic neural activity in a real environment, frequency spectrum analysis of instantaneous heartbeat variation is conceivable. According to this method, a low-frequency component (hereinafter, $HRV_{LF}$) when instantaneous heartbeats that are unequal intervals are analyzed using a frequency spectrum is interpreted as an index reflecting sympathetic neural activity and a heart vagus neural activity.

Furthermore, a high-frequency component (hereinafter, $HRV_{HF}$) when instantaneous heartbeats are analyzed using a frequency spectrum is interpreted as an index reflecting a heart vagus neural activity.

As means for measuring an ECG, a wearable device such as a Holter electrocardiograph is conceivable. In an ECG acquired using this device, measurement abnormalities occur due to electrode abnormalities including deformation and deviation of electrodes or various factors such as body motion, perspiration, and static electricity.

FIG. 10 is a diagram showing an example of measurement abnormalities in an ECG. Measurement abnormalities in an ECG can be confirmed from shapes such as noise W1 and artifacts (abnormal measurement state) W2 as shown in FIG. 10. Further, durations of the noise and artifacts change according to a duration of measurement abnormalities.

As shown in FIG. 10, waveforms observed as artifacts have frequency characteristics extremely similar to frequency characteristics of R waves, and thus it is very difficult to completely remove these waveforms through normal filtering.

Accordingly, an algorithm for extracting R waves through ECG analysis may erroneously determine artifacts as R waves and unnecessarily extract the artifacts as the R waves.

$HRV_{LF}$ and $HRV_{HF}$ reflect autonomic neural activity only in cases in which all data that is an analysis target represents a normal instantaneous heartbeat. A normal instantaneous heartbeat is an instantaneous heartbeat when both a measurement target and a measuring instrument have no abnormalities.

Abnormalities of a measurement target include the arrhythmia of an examinee, and the like. Abnormalities of a measuring instrument include states in which measurement abnormalities occur in an ECG.

Waveforms that are artifacts erroneously determined as R waves, which are a kind of measurement abnormality (such waveforms will be represented as measurement abnormality R waves below), do not completely reflect the depolarization activity of the heart from the generation mechanism thereof.

Accordingly, when at least one of a plurality of R waves constituting an instantaneous heartbeat that is an analysis target is an R wave erroneously determined from an artifact, it cannot be said that $HRV_{LF}$ or $HRV_{HF}$ reflects autonomic neural activity.

Methods for coping with measurement abnormalities of an ECG are broadly classified into two methods: reduction of the influence of measurement abnormalities according to filtering and the like; and detection of a measurement abnormality generation part.

The latter method of detecting a measurement abnormality generation part is a method which focuses on the fact that former methods of reducing the influence of measurement abnormalities according to filtering and the like could not be appropriately performed particularly when artifacts were generated and attempts to detect a measurement abnormality generation part using statistical information of ECG potential information (hereinafter referred to as conventional method a).

There are methods using a time feature quantity of an instantaneous heartbeat (refer to Non-Patent Literature 1 to 3, for example) (hereinafter referred to as conventional method b) and a method based on a measurement state and a time feature quantity of an instantaneous heartbeat (refer to Non-Patent Literature 4, for example) (hereinafter referred to as conventional method c) as methods of excluding abnormal values of an instantaneous heartbeat.

As a specific example of conventional method b, there is a method of setting threshold values to difference values between a lower limit value and an upper limit value of an instantaneous heartbeat and neighboring instantaneous heartbeat values in a time series and excluding an instantaneous heartbeat departing from the threshold values, and methods of excluding waveforms deviating from a normal distribution of an instantaneous heartbeat.

Among the methods of excluding waveforms deviating from a normal distribution of an instantaneous heartbeat, abnormal value detection according to "average of instantaneous heartbeat±standard deviation" is the simplest method, and a $2\alpha$ or $3\alpha$ rule is generally used in many cases.

As a specific example of conventional method c, there is an example of identifying a measurement state of an instantaneous heartbeat on the basis of potential amplitude information of R waves, excluding an instantaneous heartbeat identified as an abnormality, and then sequentially applying exclusion using a lower limit value and an upper limit value which is the conventional method b and $3\alpha$ rule. Here, a measurement state of an instantaneous heartbeat is evaluated on the basis of potential amplitudes of R waves constituting the instantaneous heartbeat.

CITATION LIST

Non Patent Literature

[NPL 1] Sakuma Daiki, Kanda Naoko, Yoshimi Masato, Yoshinaga Tutomu, and Irie Hidetugu, "A Real-Time Realization System at Sitting Position using Heart Rate Measurement", Multimedia, Distributed Coordination and Mobile Symposium 2013 collected papers, pp. 1188-1195, 2013

[NPL 2] Yokota Yasunari, Kawamura Yoko, Matsumaru Naoki, and Shirai Kunihito, "Monitoring of sepsis premonitories using time series of heart rate variability", Fifty-fourth automatic control alliance conference, pp. 1258-1261, 2011

[NPL 3] Eguchi Kana, Tsunoda Keisuke, Yabuuchi Tsutomu, Yoshida Kazuhiro, Watanabe Tomoki, and Mizuno Osamu, "Non-filterable noise detection method for wearable ECG devices", IEICE Technical Report, Vol. 115, No. 345, pp. 27-32, 2015

[NPL4] EguchiKana, AokiRyosuke, YoshidaKazuhiro, and Yamada Tomohiro, "Reliability Evaluation of R-R Interval Measurement Status using the Electric Potential Characteristics of QRS Complex for Wearable ECG Devices", IEICE Technical Report, Vol. 116, No. 412, pp. 171-176, 2017

SUMMARY OF THE INVENTION

Technical Problem

Although the conventional method a is a method focusing on the fact that measurement abnormalities of an ECG occur mainly due to potential differences, it uses ECG statistical information divided into two types of durations, long-term durations and short-term durations. Accordingly, a measurement state of any divided ECG is identified using statistical information of a long-term divided ECG following a long-term divided ECG including the divided ECG in a time series, and thus a time set in a long-term duration is required to identify a measurement state.

In conventional method a, when measurement abnormalities do not occur, comparative evaluation according to statistical information of a certain divided ECG and another divided ECG in a time series is performed with respect to comparison other than comparisons with a plurality of previously determined divided ECGs. Since this comparison is based on whether a potential amplitude of a certain divided ECG is an integer multiple of a potential amplitude of a divided ECG set as reference information, if measurement abnormalities are generated in the corresponding ECG, it may be difficult to reduce the influence of the measurement abnormalities.

It is difficult to dynamically set threshold values because instantaneous heartbeat values change over time. That is, when abnormal values of an instantaneous heartbeat are within a pathologically normal range, the instantaneous heartbeat cannot be generally detected as an abnormality in conventional method b.

In the above-described method of excluding waveforms deviating from a normal distribution of an instantaneous heartbeat, threshold values are set on the basis of various statistics including averages, standard deviations, median values, and quartiles because values deviating from the normal distribution are detected. Although it is necessary to calculate such statistics for a normal instantaneous heartbeat in order to identify abnormal values, a normal instantaneous heartbeat cannot be specified in this step. Accordingly, when an abnormal instantaneous heartbeat increases, the presence of such instantaneous heartbeat is regarded as normal and thus the instantaneous heartbeat cannot be detected as an abnormality.

In conventional method b, abnormalities of a measuring instrument are not considered. That is, when a duration of an instantaneous heartbeat including at least one waveform as an artifact erroneously determined as an R wave is pathologically normal or when a duration is within a normal distribution assumed for a normal instantaneous heartbeat, it is impossible to detect an abnormal instantaneous heartbeat through the conventional method.

In conventional method c, some problems of the conventional method b and problems of general filtering are solved using potential information. However, measurement abnormalities generated in an ECG do not necessarily have potential amplitude characteristics different from those of R waves. Particularly, an instantaneous heartbeat erroneously determined as R waves due to the same potential amplitude characteristics as those of R waves, such as myoelectric artifacts, cannot be detected as an abnormality.

An object of the present invention devised in view of the aforementioned circumstances is to provide an instantaneous heartbeat reliability evaluation apparatus, method, and a program which can appropriately realize identification of abnormalities of biosignals.

Means for Solving the Problem

In a first aspect of an instantaneous heartbeat reliability evaluation apparatus according to an embodiment of the present invention to accomplish the aforementioned object, the instantaneous heartbeat reliability evaluation apparatus includes: extraction means which extracts waveforms having a maximum value corresponding to depolarization of a heart in a biosignal of an examinee on the basis of a signal output from measurement means for measuring the biosignal of the examinee; first calculation means which calculates an interval between two of the waveforms neighboring in a time series and extracted by the extraction means; dividing means which divides a signal output from the measurement means into signals of predetermined periods; second calculation means which calculates feature quantities of a potential of each signal divided by the dividing means; first evaluation means which evaluates whether a measurement state of each signal divided by the dividing means is normal or abnormal on the basis of the feature quantities calculated by the second calculation means; and second evaluation means which evaluates measurement states of the two neighboring waveforms extracted by the extraction means on the basis of an evaluation result obtained by the first evaluation means and evaluates reliability of a measurement state of the interval between the waveforms calculated by the first calculation means depending on a type of the evaluated measurement states of the waveforms.

In a second aspect of the instantaneous heartbeat reliability evaluation apparatus of the present invention, in the first aspect, the second calculation means calculates at least one of a first feature quantity representing a magnitude of a potential of each of the divided signals for the signals divided by the dividing means, a second feature quantity representing variation in the potential of each of the divided signals for the signals divided by the dividing means, and a third feature quantity representing change in a time series in the potential of each of the divided signals for the signals divided by the dividing means, and the first evaluation means evaluates, on the basis of feature quantities calculated by the second calculation means with respect to a signal of an evaluation target that is one of the signals divided by the dividing means, and feature quantities calculated by the second calculation means with respect to another signal belonging to a set of signals successive in a time series including the signal of the evaluation target, whether a measurement state of the signal of the evaluation target is likely to be normal or likely to be abnormal for each of types of the feature quantities calculated by the second calculation means, and evaluates whether measurement states of the signals divided by the dividing means are normal or abnormal on the basis of an evaluation result for each feature quantity type.

In a third aspect of the instantaneous heartbeat reliability evaluation apparatus of the present invention, in the first aspect, the second calculation means calculates at least one of a first feature quantity representing a magnitude of a potential of each of the divided signals for the signals divided by the dividing means, a second feature quantity representing variation in the potential of each of the divided signals for the signals divided by the dividing means, and a third feature quantity representing change in a time series in the potential of each of the divided signals for the signals divided by the dividing means, and the first evaluation means evaluates, on the basis of feature quantities calculated by the second calculation means with respect to a signal of an evaluation target that is one of the signals divided by the dividing means, and feature quantities calculated by the second calculation means with respect to a signal neighboring the signal of the evaluation target in a time series, whether a measurement state of the signal of the evaluation target is likely to be normal or likely to be abnormal for each of types of the feature quantities calculated by the second calculation means, and evaluates whether measurement states of the signals divided by the dividing means are normal or abnormal on the basis of an evaluation result for each feature quantity type.

In a fourth aspect of the instantaneous heartbeat reliability evaluation apparatus of the present invention, in the first aspect, the second calculation means calculates at least one of a first feature quantity representing a magnitude of a potential of each of the divided signals for the signals divided by the dividing means, a second feature quantity representing variation in the potential of each of the divided signals for the signals divided by the dividing means, and a third feature quantity representing change in a time series in the potential of each of the divided signals for the signals divided by the dividing means, and the first evaluation means evaluates, on the basis of feature quantities calculated by the second calculation means with respect to a signal of an evaluation target that is one of the signals divided by the dividing means, and feature quantities calculated by the second calculation means with respect to a signal for which a measurement state has been evaluated as normal in advance among the signals divided by the dividing means, whether a measurement state of the signal of the evaluation target is likely to be normal or likely to be abnormal for each of types of the feature quantities calculated by the second calculation means, and evaluates whether measurement states of the signals divided by the dividing means are normal or abnormal on the basis of an evaluation result for each feature quantity type.

In a fifth aspect of the instantaneous heartbeat reliability evaluation apparatus of the present invention, in the first aspect, the second calculation means calculates at least one of a first feature quantity representing a magnitude of a potential of each of the divided signals for the signals divided by the dividing means, a second feature quantity representing variation in the potential of each of the divided signals for the signals divided by the dividing means, and a third feature quantity representing change in a time series in the potential of each of the divided signals for the signals divided by the dividing means, and the first evaluation means acquires, on the basis of feature quantities calculated by the second calculation means with respect to a signal of an evaluation target that is one of the signals divided by the dividing means, and feature quantities calculated by the second calculation means with respect to another signal belonging to a set of signals successive in a time series including the signal of the evaluation target, a first evaluation result representing whether a measurement state of the signal of the evaluation target is likely to be normal or likely to be abnormal for each of types of the feature quantities calculated by the second calculation means, acquires a second evaluation result representing whether a measurement state of the signal of the evaluation target is likely to be normal or likely to be abnormal for each of types of the feature quantities calculated by the second calculation means on the basis of feature quantities calculated by the second calculation means with respect to the signal of the evaluation target that is one of the signals divided by the dividing mean, and feature quantities calculated by the second calculation means with respect to a signal neighboring the signal of the evaluation target in a time series, acquires a third evaluation result representing whether a measurement state of the signal of the evaluation target is likely to be normal or likely to be abnormal for each of types of the feature quantities calculated by the second calculation means on the basis of feature quantities calculated by the second calculation means with respect to the signal of the evaluation target, and feature quantities calculated by the second calculation means with respect to a signal for which a measurement state has been evaluated as normal in advance, and evaluates the measurement state of the signal of the evaluation target as abnormal when at least one of the first, second and third evaluation results represents that the measurement state of the signal of the evaluation target is likely to be abnormal.

In a sixth aspect of the instantaneous heartbeat reliability evaluation apparatus of the present invention, in the first aspect, the second evaluation means evaluates the measurement states of the waveforms extracted by the extraction means as abnormal from a signal for which a measurement state has been evaluated as abnormal by the first evaluation means, and evaluates the measurement states of the waveforms extracted by the extraction means as normal from a signal for which a measurement state has been evaluated as normal by the first evaluation means.

An aspect of an instantaneous heartbeat reliability evaluation method performed by an instantaneous heartbeat reliability evaluation apparatus according to an embodiment of the present invention includes: extracting waveforms having a maximum value corresponding to depolarization of a heart in a biosignal of an examinee; calculating an interval between two of the extracted waveforms neighboring in a time series; dividing the biosignal into signals of predetermined periods; calculating feature quantities of a potential of each of the divided signals; evaluating whether a measurement state of each of the divided signals is normal or abnormal on the basis of the calculated feature quantities; evaluating measurement states of the two neighboring extracted waveforms on the basis of an evaluation result of a measurement state of each of the divided signals; and evaluating reliability of a measurement state of the calculated interval between the waveforms depending on a type of the evaluated measurement states of the waveforms.

An aspect of an instantaneous heartbeat reliability evaluation processing program according to an embodiment of the present invention causes a processor to function as each means of the instantaneous heartbeat reliability evaluation apparatus according to any one of the first to sixth aspects.

Effects of the Invention

According to the first aspect of the instantaneous heartbeat reliability evaluation apparatus according to an embodiment of the present invention, a measurement state of an interval between waveforms having a maximum value corresponding to depolarization of a heart is evaluated on the basis of evaluation results of measurement states of divided biosignals, and thus it is possible to reduce the influence of a measurement state of a biosignal on evaluation of the measurement state of the interval between the waveforms having the maximum value corresponding to depolarization of the heart.

According to the second aspect of the instantaneous heartbeat reliability evaluation apparatus according to an embodiment of the present invention, it is evaluated whether measurement states of divided signals are likely to be normal or abnormal for each feature quantity type and it is evaluated whether the measurement states of the divided signals are normal or abnormal on the basis of an evaluation result for each feature quantity type, and thus it is possible to improve the accuracy of evaluation of a measurement state of a biosignal.

According to the third to fifth aspects of the instantaneous heartbeat reliability evaluation apparatus according to an embodiment of the present invention, a measurement state of a signal that is an evaluation target is evaluated on the basis of feature quantities of signals positioned before and after the evaluation target signal in a time series or a signal for which a measurement state has been evaluated as normal in advance, and thus it is possible to reduce a time taken to evaluate a measurement state calculated with respect to the evaluation target signal that is one of divided signals.

According to the sixth aspect of the instantaneous heartbeat reliability evaluation apparatus according to an embodiment of the present invention, measurement states of waveforms having a maximum value corresponding to depolarization of a heart are evaluated on the basis of an evaluation result of a measurement state of a biosignal that is an evaluation target, and thus it is possible to appropriately evaluate the measurement states of the waveforms having the maximum value corresponding to depolarization of the heart on the basis of feature quantities of potentials of signals divided from the biosignal.

That is, according to the present invention, it is possible to realize appropriate biosignal abnormality identification.

DESCRIPTION OF EMBODIMENTS

Hereinafter, an embodiment pertaining to the present invention will be described with reference to the drawings.

In an embodiment of the present invention, the reliability of an instantaneous heartbeat is evaluated on the basis of potential information of two R waves constituting the instantaneous heartbeat.

Here, identification of abnormalities in a target instantaneous heartbeat is realized by separately analyzing an ECG measurement state in advance and assigning information on the measurement state to the R waves constituting the instantaneous heartbeat.

Here, an embodiment of the present invention uses a method that reduces the influence of measurement abnormalities while reducing a waiting time taken to identify the measurement abnormalities which is a problem in the aforementioned conventional method a.

Further, in evaluation of an instantaneous heartbeat, potential amplitude information of R waves described in the aforementioned conventional method c or time information described in the aforementioned conventional method b may be considered.

(Configuration)

Figure 1:
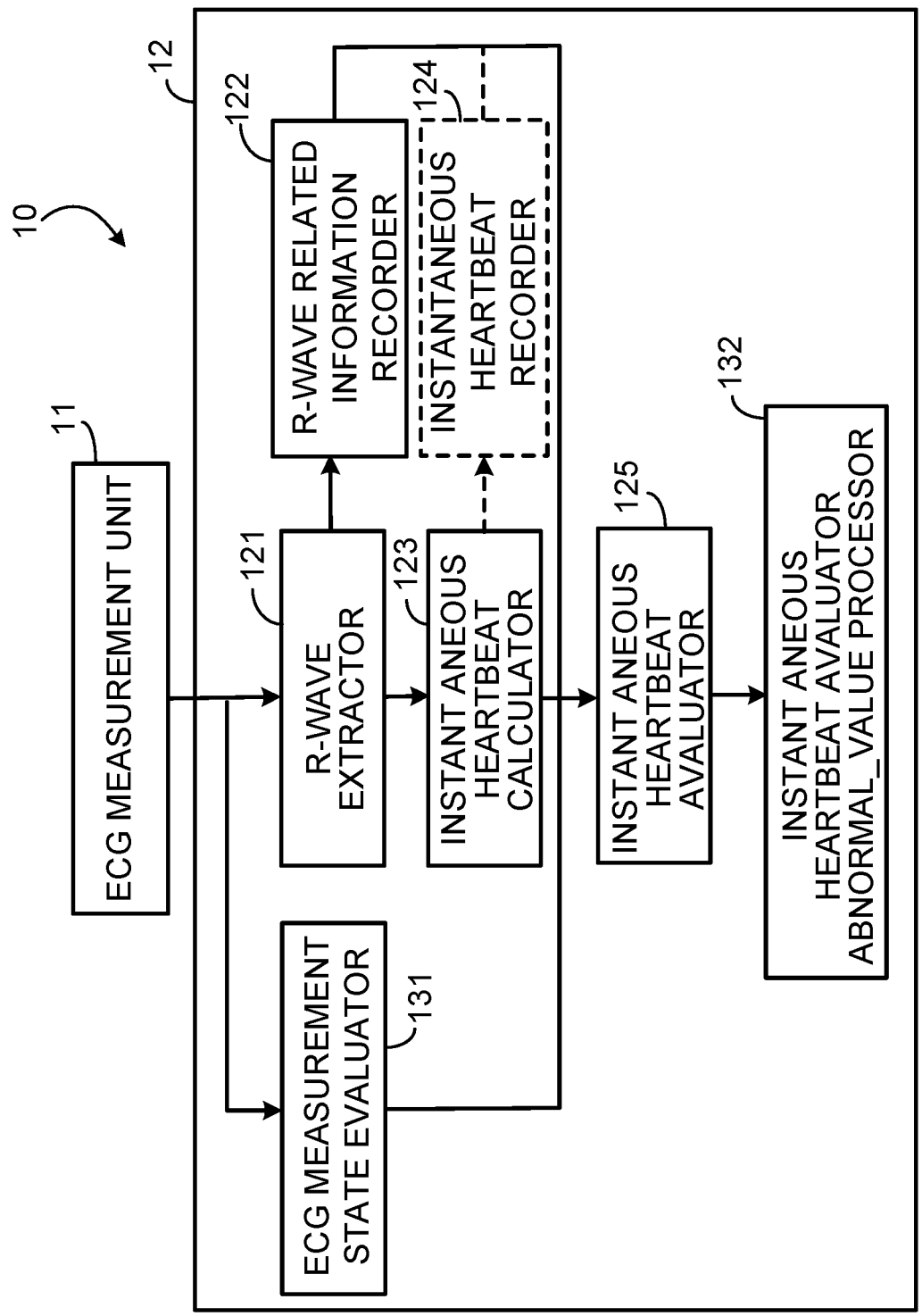
FIG. 1 is a diagram showing a configuration example of an instantaneous heartbeat reliability evaluation apparatus according to an embodiment of the present invention.

FIG. 1 is a diagram showing a configuration example of an instantaneous heartbeat reliability evaluation apparatus according to an embodiment of the present invention. The instantaneous heartbeat reliability evaluation apparatus 10 shown in FIG. 1 includes an ECG measurement unit 11 and an instantaneous heartbeat reliability evaluation unit 12.

As an example, in the instantaneous heartbeat reliability evaluation apparatus 10, the ECG measurement unit 11 is used as a wearable device that can be worn by an examinee (user) and the instantaneous heartbeat reliability evaluation unit 12 is realized by a system using a computer device such as a smartphone, a tablet type terminal, or a personal computer (PC).

For example, the computer device includes a processor such as a central processing unit (CPU), a memory connected to the processor, and a communication interface for communicating with the ECG measurement unit 11 (wirelessly, for example). The memory is configured as a storage device including a storage medium such as a nonvolatile memory.

Meanwhile, the realization form of the instantaneous heartbeat reliability evaluation apparatus 10 is not limited to this example. For example, the instantaneous heartbeat reliability evaluation apparatus 10 may be realized by a single device. Further, the ECG measurement unit 11 may be provided outside the instantaneous heartbeat reliability evaluation apparatus 10. In other words, the instantaneous heartbeat reliability evaluation apparatus 10 may acquire an electrocardiographic measurement result of an examinee from an external electrocardiographic measurement apparatus corresponding to the ECG measurement unit 11.

An embodiment of the present invention differs from conventional technologies in that an ECG measurement state analyzed in advance is used when an instantaneous heartbeat is evaluated on the basis of potential information of two R waves constituting the instantaneous heartbeat.

The ECG measurement unit 11 measures an ECG of an examinee and transmits a measurement result to the instantaneous heartbeat reliability evaluation unit 12. An electrocardiogram is a biosignal of the circulatory system and includes, for example, a periodic signal synchronized with ventricular contractions. The ECG measurement unit 11 measures an electrocardiogram sing at least two electrodes.

The measurement result includes data from which an electrocardiogram corresponding to R waves in the ECG can be extracted. For example, the measurement result includes data of the ECG.

It is desirable that the ECG measurement unit 11 be able to measure electrocardiographic waveforms corresponding to R waves irrespective of the realization form thereof. For example, the ECG measurement unit 11 is configured as a Holter electrocardiograph.

The instantaneous heartbeat reliability evaluation unit 12 receives the measurement result from the ECG measurement unit 11 and evaluates the reliability of an instantaneous heartbeat of the examinee on the basis of the received measurement result.

For example, the instantaneous heartbeat reliability evaluation unit 12 includes an R-wave extractor 121, an R-wave related information recorder 122, an instantaneous heartbeat calculator 123, an instantaneous heartbeat recorder 124, an instantaneous heartbeat evaluator 125, an ECG measurement state evaluator 131, and an instantaneous heartbeat abnormal value processor 132.

Functions of the R-wave extractor 121, the R-wave related information recorder 122, the instantaneous heartbeat calculator 123, the instantaneous heartbeat recorder 124, the instantaneous heartbeat evaluator 125, the ECG measurement state evaluator 131, and the instantaneous heartbeat abnormal value processor 132 are realized, for example, by a processor reading and executing a program stored in a memory. Further, some or all of these functions may be realized by a circuit such as an application-specific integrated circuit (ASIC).

Figure 2:
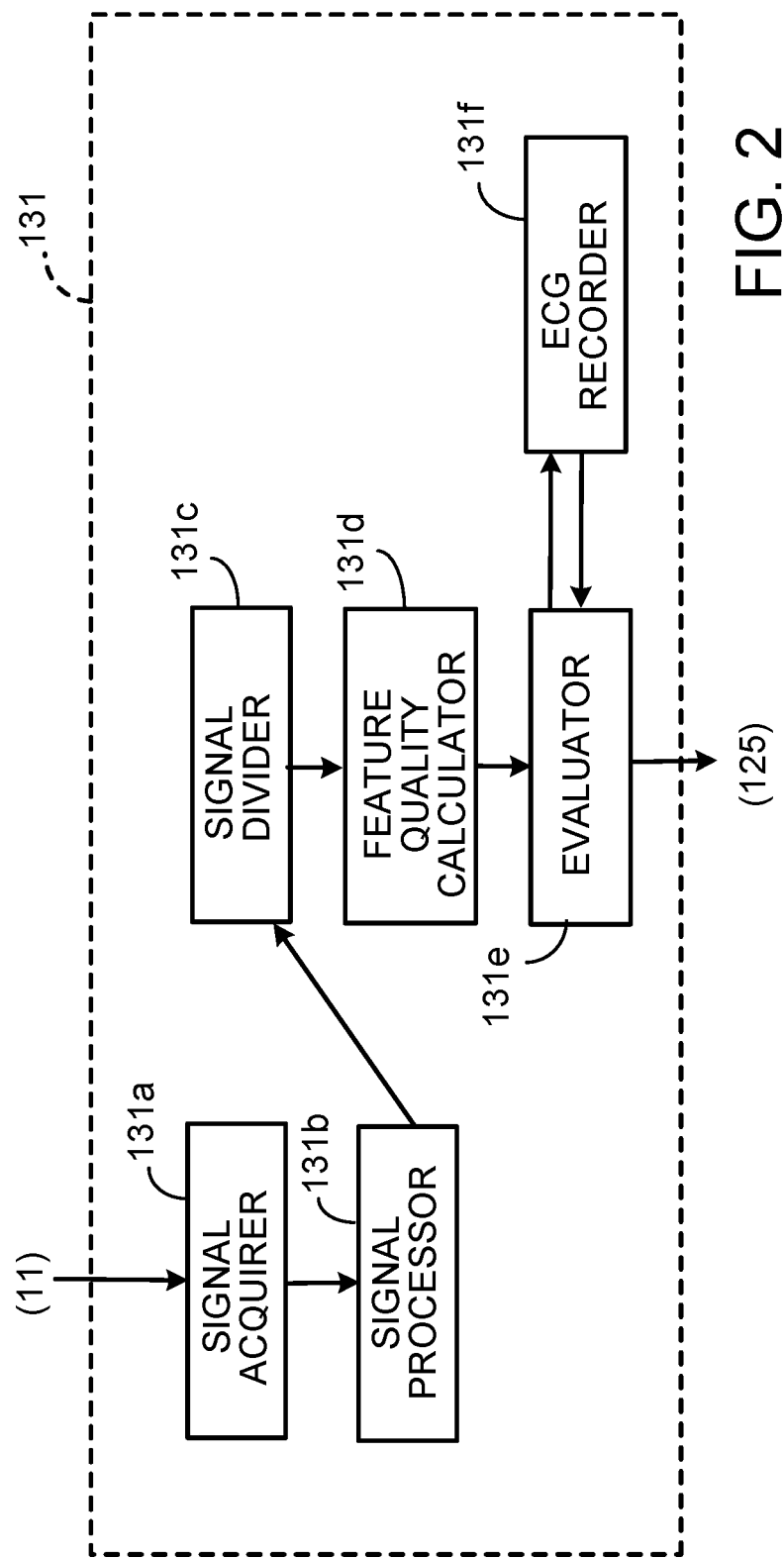
FIG. 2 is a diagram showing a configuration example of an ECG measurement state evaluator of the instantaneous heartbeat reliability evaluation apparatus according to an embodiment of the present invention.

The ECG measurement state evaluator 131 evaluates an ECG measurement state. FIG. 2 is a diagram showing a configuration example of the ECG measurement state evaluator of the instantaneous heartbeat reliability evaluation apparatus according to an embodiment of the present invention.

As shown in FIG. 2, the ECG measurement state evaluator 131 includes a signal acquirer 131a, a signal preprocessor 131b, a signal divider 131c, a feature quantity calculator 131d, an evaluator 131e, and an ECG recorder 131f. A specific realization example of each component will be described later.

Each component of the instantaneous heartbeat reliability evaluation unit 12 will be described. The R-wave extractor 121 analyzes an ECG acquired through the ECG measurement unit 11 and extracts R waves. In addition, the R-wave extractor 121 records information on the extracted R waves in the R-wave related information recorder 122.

The R-wave related information recorder 122 is essential when R-wave measurement state identification based on potential amplitude information of R waves is used simultaneously. The R-wave related information recorder 122 includes a storage medium such as a nonvolatile memory and records information on the R waves extracted by the R-wave extractor 121 in the storage medium. Although information by which at least two types of R-wave measurement states including a normal measurement state and artifacts states are distinguishable is a target of recording on the R-wave related information recorder 122 in an embodiment of the present invention, other information is not particularly limited.

For example, information on a time at which the extracted R waves have appeared may be a target of recording on the R-wave related information recorder 122. Further, a specific recording format is not particularly limited.

The instantaneous heartbeat calculator 123 calculates an instantaneous heartbeat that is an interval between R waves neighboring in a time series on the basis of the R waves extracted by the R-wave extractor 121. The instantaneous heartbeat calculator 123 records information on the calculated instantaneous heartbeat in the instantaneous heartbeat recorder 124.

The instantaneous heartbeat recorder 124 includes a storage medium such as a nonvolatile memory and records information on the instantaneous heartbeat calculated by the instantaneous heartbeat calculator 123 in the storage medium.

Although a specific recording format in the instantaneous heartbeat recorder 124 is not particularly limited, for example, (1) a matrix of an instantaneous heartbeat and (2) a data matrix composed of time information of the first R wave constituting an instantaneous heartbeat and the instantaneous heartbeat are conceivable.

The function of the instantaneous heartbeat recorder 124 is not an essential function in an embodiment of the present invention. This function is necessary only when the instantaneous heartbeat reliability evaluation unit 12 evaluates an instantaneous heartbeat in consideration of time information of the instantaneous heartbeat in addition to an ECG measurement state and potential information of R waves.

The instantaneous heartbeat evaluator 125 evaluates the reliability of the instantaneous heartbeat calculated by the instantaneous heartbeat calculator 123 on the basis of information recorded in the R-wave related information recorder 122. A specific evaluation method will be described in the following operation example.

Operation Example

An operation example of an embodiment of the present invention will be described. In this operation example, for artifacts that are difficult to identify through potential amplitude characteristics of R waves, a method of excluding an instantaneous heartbeat for which the artifacts are erroneously determined as an abnormal value will be described.

Figure 3:
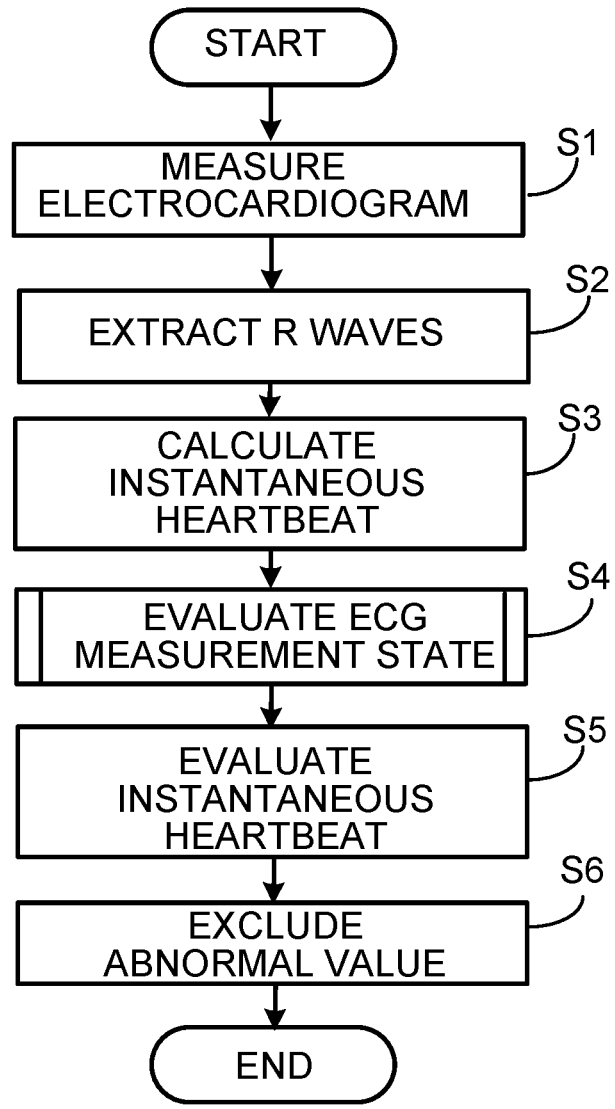
FIG. 3 is a flowchart showing an example of a processing procedure performed by the instantaneous heartbeat reliability evaluation apparatus according to an embodiment of the present invention.

A specific processing procedure is described below. FIG. 3 is a flowchart showing an example of a processing procedure performed by the instantaneous heartbeat reliability evaluation apparatus according to an embodiment of the present invention.

The ECG measurement unit 11 measures an ECG using at least two electrodes (S1).

The R-wave extractor 121 extracts R waves from the ECG measured by the ECG measurement unit 11 (S2). When potential amplitudes of R waves are used as in the aforementioned conventional method c, the R-wave extractor 121 records potential information of the extracted R waves in the R-wave related information recorder 122.

The instantaneous heartbeat calculator 123 calculates an instantaneous heartbeat from two R waves neighboring in a time series on the basis of the R waves extracted by the R-wave extractor 121 (S3).

When a measurement state of an instantaneous heartbeat is evaluated in consideration of time information of the instantaneous heartbeat as in the aforementioned conventional method b, the instantaneous heartbeat calculator 123 records information on the calculated instantaneous heartbeat in the instantaneous heartbeat recorder 124.

Figure 4:
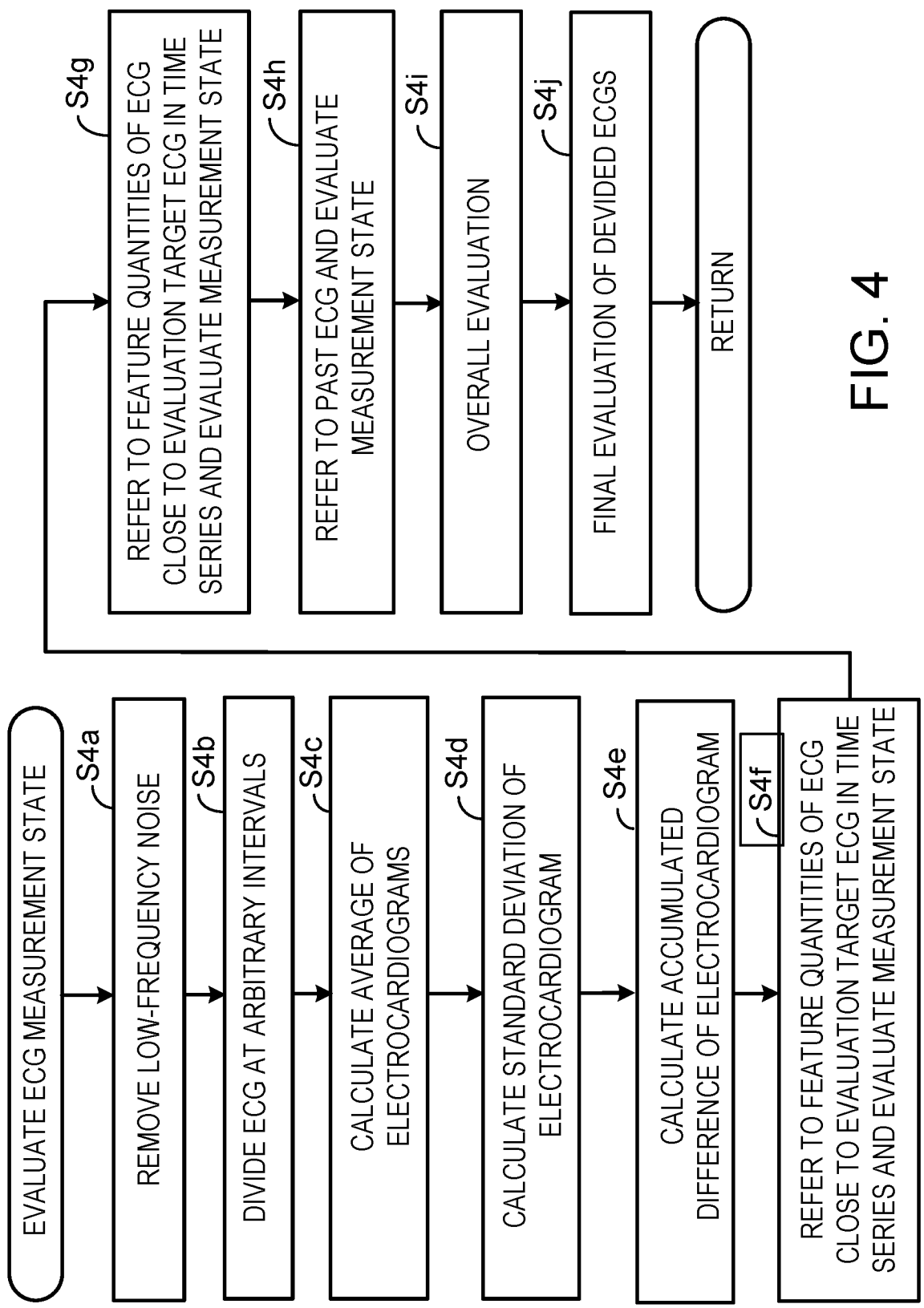
FIG. 4 is a flowchart showing an example of a processing procedure for evaluation of ECG measurement states performed by the instantaneous heartbeat reliability evaluation apparatus according to an embodiment of the present invention.

The ECG measurement state evaluator 131 evaluates the measurement state of the ECG on the basis of the ECG measured by the ECG measurement unit 11 (S4). S4 will be described in detail below. FIG. 4 is a flowchart showing an example of a processing procedure for evaluation of an ECG measurement state performed by the instantaneous heartbeat reliability evaluation apparatus according to an embodiment of the present invention.

The signal acquirer 131a of the ECG measurement state evaluator 131 acquires a signal of an ECG measured by the ECG measurement unit 11. The signal preprocessor 131b removes low-frequency noise included in the signal of the ECG acquired by the signal acquirer 131a (S4a).

Figure 9:
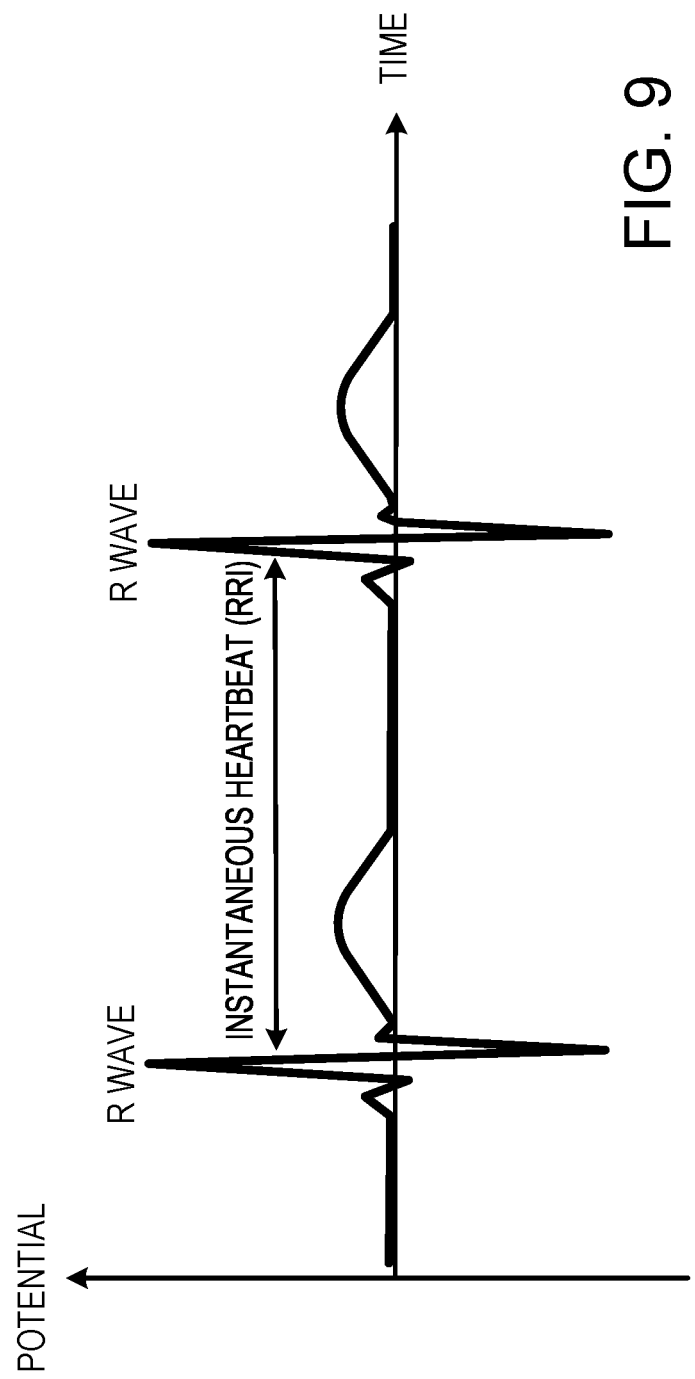
FIG. 9 is a diagram showing an example of an instantaneous heartbeat.
Figure 10:
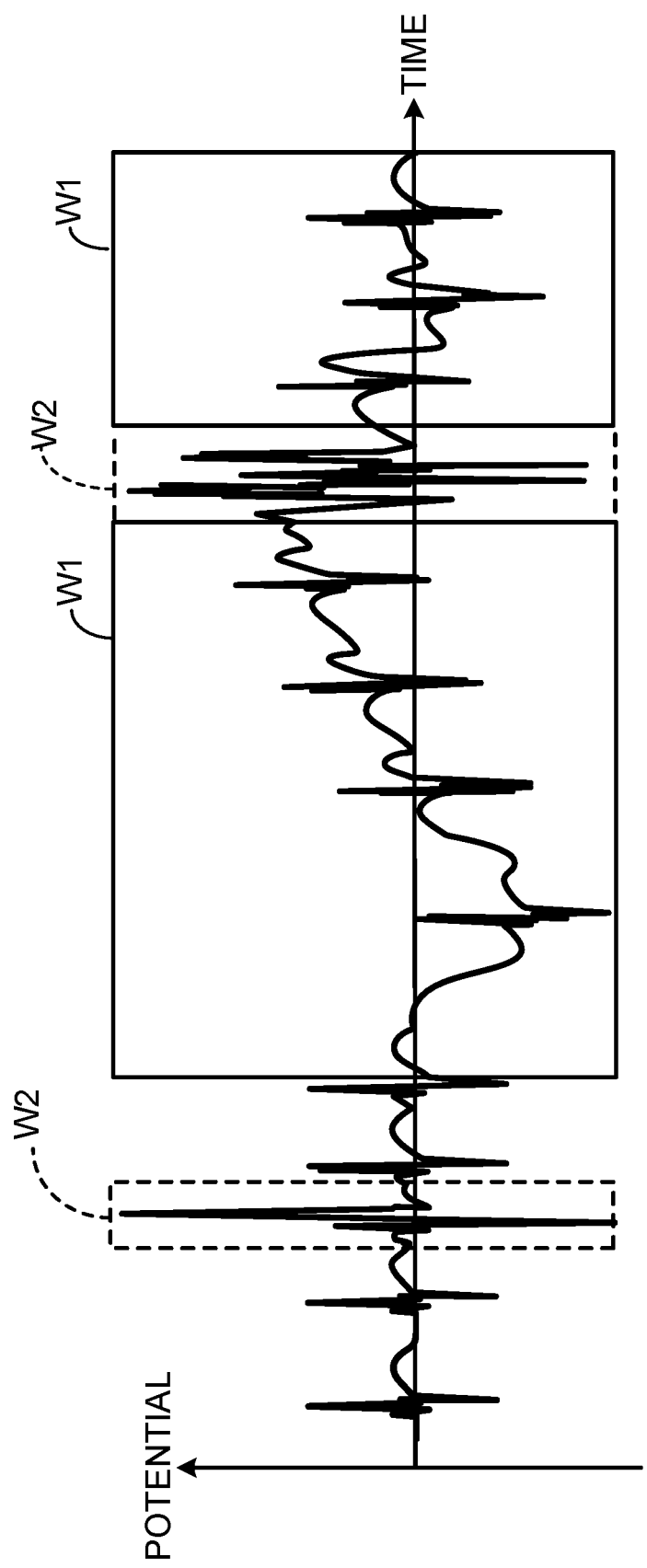
FIG. 10 is a diagram showing an example of measurement abnormalities in an ECG.

This process may use any realization means as long as it is a method that can remove low-frequency baseline fluctuations represented as noise in FIG. 9.

As an example, a high pass filter having a fixed cutoff frequency, a variable bandpass filter according to removal of a spectral envelope or the like through Cepstrum analysis, and the like are conceivable as realization means that can remove low-frequency noise.

Figure 5:
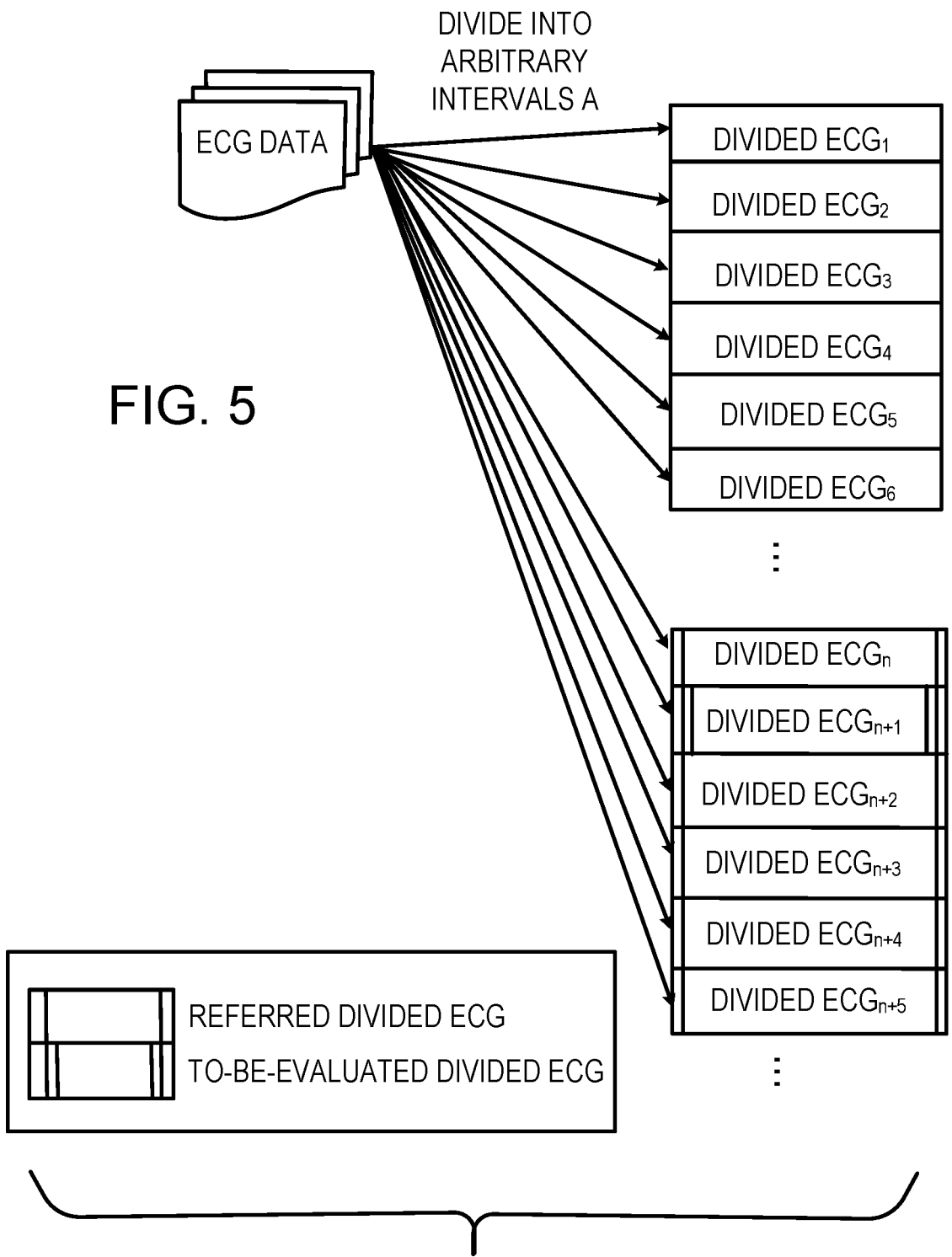
FIG. 5 is a diagram showing an example of division of an ECG and a first example of ECG measurement state evaluation performed by the instantaneous heartbeat reliability evaluation apparatus according to an embodiment of the present invention.

The signal divider 131c of the ECG measurement state evaluator 131 divides an ECG signal into a plurality of periods including at least one period. FIG. 5 is a diagram showing an example of division of an ECG and a first example of ECG measurement state evaluation performed by the instantaneous heartbeat reliability evaluation apparatus according to an embodiment of the present invention.

Specifically, the signal divider 131c divides an ECG as an evaluation target at arbitrary intervals A that are arbitrary time intervals (S4b).

In S4b, the signal divider 131c divides the ECG signal into a plurality of divided ECGs having data at the arbitrary intervals A, for example, a divided $ECG_1$, divided $ECG_2$, divided $ECG_3$, divided $ECG_4$, divided $ECG_5$, divided $ECG_6$, ..., divided $ECG_n$, divided $ECG_{n+1}$, divided $ECG_{n+2}$, divided $ECG_{n+3}$, divided $ECG_{n+4}$, and divided $ECG_{n+5}$ shown in FIG. 5.

Here, each of the plurality of divided ECGs can be regarded as a packet that is one unit of the ECG signal.

In the ECG measurement state evaluator 131, an ECG segmented for each arbitrary interval A becomes a minimum evaluation unit in the following.

That is, when an ECG in a certain arbitrary interval A is determined as a measurement abnormality, the ECG measurement state evaluator 131 regards all ECGs included in divided regions of the ECG as measurement abnormalities.

Although a specific length of the arbitrary interval A is not particularly designated here, it is desirable that the numbers of R waves observed in arbitrary intervals A be approximately equal in the respective divided ECGs.

For example, it is conceivable to set a set value of the arbitrary interval A to 1.5 [sec] that is a maximum RRI of a healthy person, or the like such that at least single R wave is observed in divided ECGs.

The feature quantity calculator 131d of the ECG measurement state evaluator 131 calculates various feature quantities with respect to ECGs divided at the arbitrary intervals A.

Meanwhile, various feature quantities represented below are exemplary, and different types of feature quantities may be added or other types of feature quantities having the same characteristics may be used instead, but the feature quantities need to represent different values in a measurement abnormality state and a normal state.

With respect to each ECG divided in this manner, calculation of various feature quantities is guided on the basis of the fact that an electrocardiogram is a biosignal in which similar waveforms repeatedly appear.

Accordingly, when an ECG is segmented for each arbitrary interval and a measurement state of each ECG is evaluated for each arbitrary interval, it is conceivable that cardiac potential levels, variations, and change quantities of waveforms which are various feature quantities represented below represent similar values in any arbitrary interval regions in an ideal state in which noise having frequency characteristics similar or identical to frequency characteristics of the electrocardiogram that is a target, for example, a similar or identical frequency band (hereinafter referred to as "similar frequency characteristic noise") is not mixed.

Calculation of feature quantities will be described in detail.

Firstly, the feature quantity calculator 131d calculates the average of absolute values of potentials of electrocardiograms included in divided ECGs as a feature quantity a (S4c).

Meanwhile, this feature quantity a may be another feature quantity if it is a positive value that can broadly represent a magnitude relation of "magnitudes of electrocardiographic waveforms".

This feature quantity a allows identification of measurement abnormalities based on the magnitudes of potentials of electrocardiograms.

Secondly, the feature quantity calculator 131d calculates a standard deviation with respect to electrocardiograms included in the divided ECGs as a feature quantity b (S4d).

Meanwhile, this feature quantity b may be another statistic quantity such as a variance value that can be calculated for each specific interval, for example, if it is a value that can broadly represent "variation in electrocardiographic waveforms".

It is possible to evaluate the number of pieces of electrocardiographic data representing values deviating from the average due to similar frequency characteristic noise or the amount of deviation from the average using the feature quantity b. Accordingly, identification of measurement abnormalities based on variation in the potentials of electrocardiograms can be performed.

Thirdly, the feature quantity calculator 131d calculates an accumulated value of differences (hereinafter referred to as an accumulated difference) as a feature quantity c with respect to electrocardiograms included in divided ECGs or the absolute value of the electrocardiograms (S4e).

Meanwhile, this feature quantity c may be another statistic quantity such as a moving average or an integrated value of differentiation which can be calculated for each specific interval, for example, if it is a value that can broadly represent "change quantity of electrocardiographic waveforms" in a time series.

The feature quantity calculator 131d can evaluate an abnormality that is difficult to be locally detected, such as an abnormality having a small value and generated over a long term, for example, using the feature quantity c. Accordingly, identification of measurement abnormalities based on a change quantity of the potentials of electrocardiograms can be performed.

Although cases in which feature quantities representing "the magnitudes of electrocardiographic waveforms", "variation in electrocardiographic waveforms" and "change quantity of electrocardiographic waveforms" are sequentially calculated have been described in [0059] to [0061], the sequence of calculation of the feature quantities is not particularly designated in the present embodiment.

That is, the feature quantities may be calculated in parallel or may be calculated in a different order from that described in [0059] to [0061].

The evaluator 131e of the ECG measurement state evaluator 131 evaluates a measurement state of a corresponding divided ECG using the feature quantities a, b and c respectively calculated in S4c, S4d and S4e.

Here, a case in which the average, the standard deviation and the accumulated difference respectively represented in S4c, S4d and S4e are used as feature quantities is described.

When the evaluator 131e evaluates a to-be-evaluated divided ECG that is a certain divided ECG as an evaluation target, for example, the divided $ECG_{n+1}$ shown in FIG. 5, the evaluator 131e evaluates the to-be-evaluated divided ECG through the following processes i, ii and iii with reference to divided ECGs positioned near the ECG or the like in a time series.

Meanwhile, the processes i, ii and iii described below are independently performed for each feature quantity type. In addition, since the execution order of the processes i, ii and iii is not fixed in the present embodiment, the processes may be realized by parallel processing or the like.

i) The process i will be described. In the process i, the evaluator 131e refers to feature quantities of i divided ECGs positioned near a to-be-evaluated divided ECG as an evaluation target, for example, the divided $ECG_{n+1}$ shown in FIG. 5, in a time series for a certain type of feature quantity.

To appropriately detect measurement abnormalities of divided ECGs while reducing a waiting time more than in conventional methods, the evaluator 131e evaluates a measurement state of any to-be-evaluated divided ECG, for example, the divided $ECG_{n+1}$ of FIG. 5, with reference to divided ECGs of a cluster to which the to-be-evaluated divided ECG belongs (referred divided ECGs), for example, the divided $ECG_n$, divided $ECG_{n+2}$, divided $ECG_{n+3}$, divided $ECG_{n+4}$, and divided $ECG_{n+5}$ shown in FIG. 5, as shown in FIG. 5 (S4f).

That is, in the process i, the measurement state of the to-be-evaluated divided ECG is evaluated with reference to other divided ECGs belonging to a set of divided ECGs including the to-be-evaluated divided ECGs and consecutive in a time series.

Here, when the values calculated in S4c and S4d are represented as the average y and the standard deviation a of potentials of the referred divided ECGs, the evaluator 131e evaluates the measurement state of the to-be-evaluated divided ECG using the following expression (1).

The left side of the expression (1) is a feature quantity calculated with respect to the to-be-evaluated divided ECG. The right side of the expression (1) is the average y and the standard deviation a of the potentials of the referred divided ECGs.

Accordingly, even if a measurement state of any referred divided ECG is abnormal, the influence of this abnormality can be reduced.

$$\text{Statistics}_{target} \leq \mu_{ref} + k \times \sigma_{ref} \qquad \text{Expression (1)}$$

When the condition represented by the expression (1) is satisfied, the evaluator 131e regards change in feature quantities calculated with respect to the to-be-evaluated divided ECG as belonging to values within a predetermined range in a broad sense and determines the to-be-evaluated divided ECG as normal data. Then, the evaluator 131e assigns $TRUE_i$ to the to-be-evaluated divided ECG used to calculate the aforementioned feature quantities.

Figure 6:
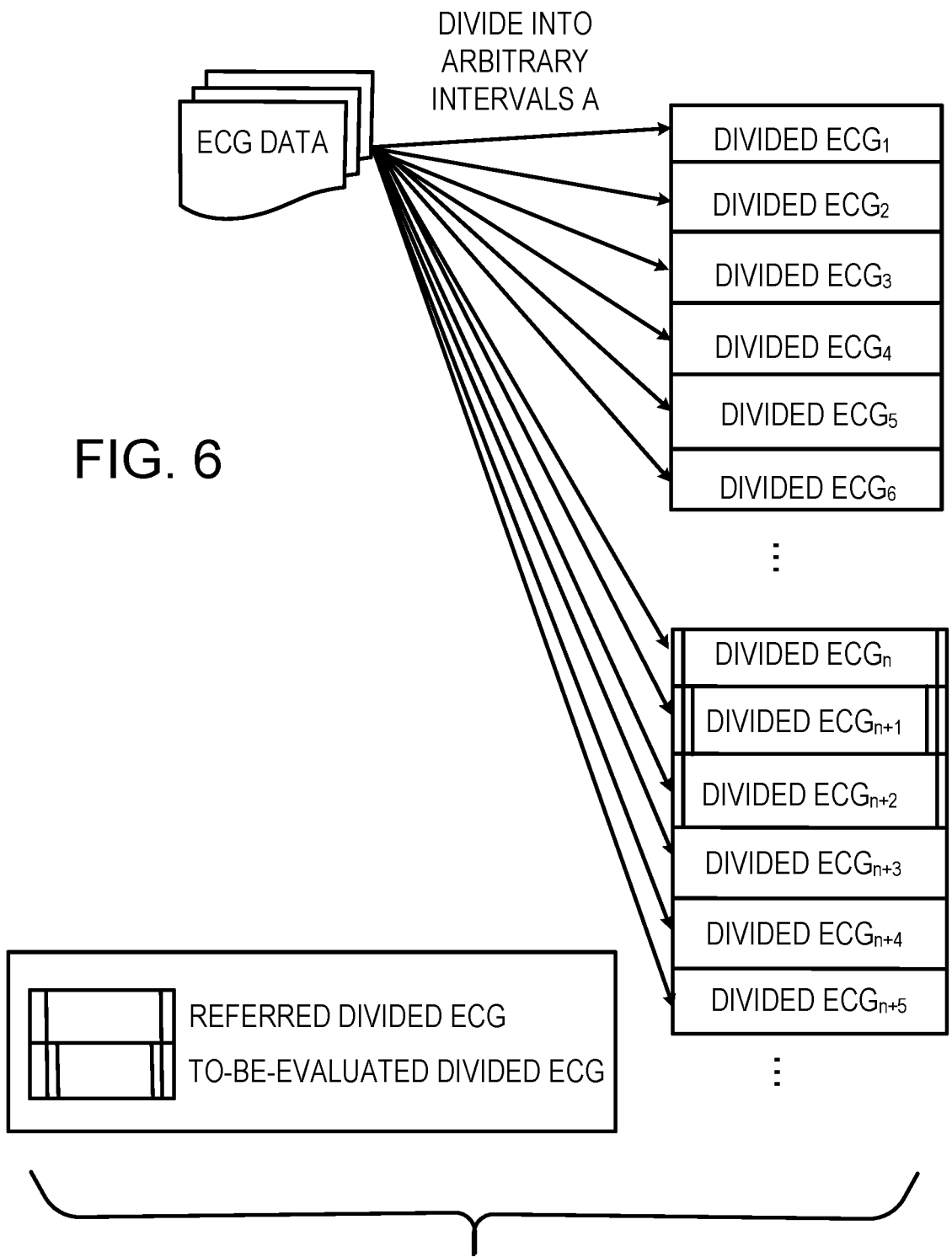
FIG. 6 is a diagram showing a second example of ECG measurement state evaluation performed by the instantaneous heartbeat reliability evaluation apparatus according to an embodiment of the present invention.

On the other hand, when the condition represented by the expression (1) is not satisfied, the evaluator 131e evaluates that measurement abnormalities are likely to be generated in the to-be-evaluated divided ECG and assigns $FALSE_i$ to the to-be-evaluated divided ECG used to calculate the feature quantities according to this evaluation. Assignment of $TRUE_i$ and $FALSE_i$ is independently performed for each feature quantity type as described above.

ii) The process ii will be described. FIG. 6 is a diagram showing a second example of ECG measurement state evaluation performed by the instantaneous heartbeat reliability evaluation apparatus according to an embodiment of the present invention.

To appropriately detect measurement abnormalities of divided ECGs while reducing a waiting time more than in conventional methods, the evaluator 131e evaluates a measurement state of a to-be-evaluated divided ECG as an evaluation target with reference to j divided ECGs neighboring in a time series with respect to the divided $ECG_{n+1}$ of FIG. 6, for example, the divided $ECG_n$ and divided $ECG_{n+2}$ of FIG. 5, as shown in FIG. 6, with respect to a certain type of feature quantity in the process ii (S4g). Accordingly, the evaluator 131e appropriately identifies points in time near starting and end points in time of measurement abnormalities. Here, even if a measurement state of any referred divided ECG is abnormal, the evaluator 131e attempts to reduce the influence of the abnormality by evaluating the measurement state of the to-be-evaluated divided ECG using the expression (1) as in the process i.

When the condition represented by the expression (1) is satisfied, the evaluator 131e regards change in feature quantities calculated with respect to the to-be-evaluated divided ECG as belonging to values within a predetermined range in a broad sense and determines the to-be-evaluated divided ECG as normal data. Then, the evaluator 131e assigns $TRUE_{ii}$ to the to-be-evaluated divided ECG used to calculate the feature quantities.

Figure 7:
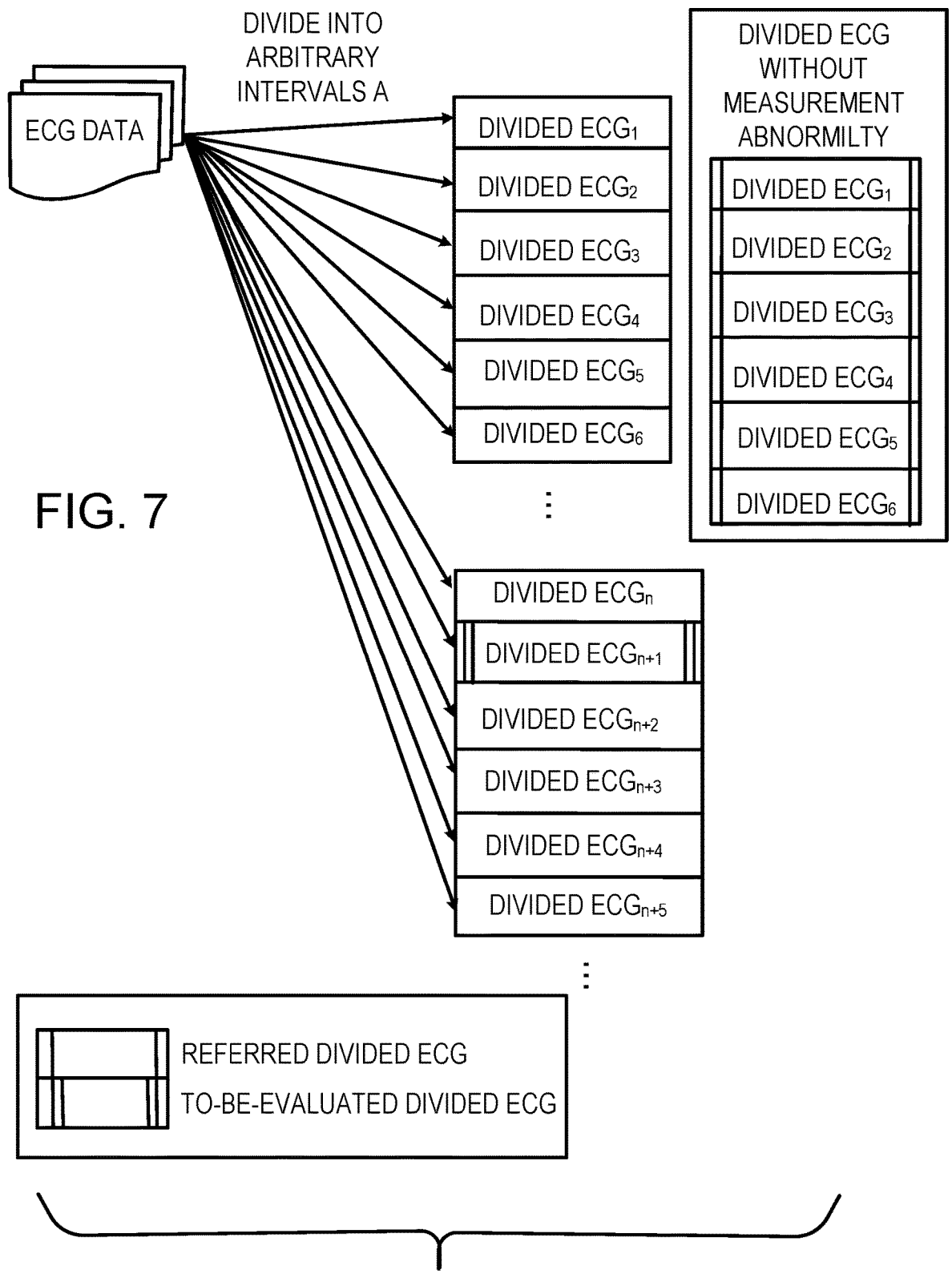
FIG. 7 is a diagram showing a third example of ECG measurement state evaluation performed by the instantaneous heartbeat reliability evaluation apparatus according to an embodiment of the present invention.

On the other hand, when the condition represented by the expression (1) is not satisfied, the evaluator 131e evaluates that measurement abnormalities are likely to be generated in the to-be-evaluated divided ECG and assigns $FALSE_{ii}$ to the to-be-evaluated divided ECG used to calculate the feature quantities according to this evaluation. Assignment of $TRUE_{ii}$ and $FALSE_{ii}$ is independently performed for each feature quantity type as described above.

iii) The process iii will be described. FIG. 7 is a diagram showing a third example of ECG measurement state evaluation performed by the instantaneous heartbeat reliability evaluation apparatus according to an embodiment of the present invention.

To appropriately detect measurement abnormalities of divided ECGs while reducing a waiting time more than in conventional methods, the evaluator 131e evaluates a measurement state of a to-be-evaluated divided ECG using the expression (1) as in the process i and the process ii with reference to feature quantities of k past divided ECGs regarded as "normal" in advance in a process of S4j which will be described later from the ECG recorder 131f with respect to a certain type of feature quantity in the process iii (S4h).

When the condition represented by the expression (1) is satisfied, the evaluator 131e regards change in feature quantities calculated with respect to the to-be-evaluated divided ECG as belonging to values within a predetermined range in a broad sense and determines the to-be-evaluated divided ECG as normal data. Then, the evaluator 131e assigns $TRUE_{iii}$ to the to-be-evaluated divided ECG used to calculate the feature quantities.

On the other hand, when the condition represented by the expression (1) is not satisfied, the evaluator 131e evaluates that measurement abnormalities are likely to be generated in the to-be-evaluated divided ECG and assigns $FALSE_{iii}$ to the to-be-evaluated divided ECG used to calculate the feature quantities according to this evaluation. Assignment of $TRUE_{ii}$ and $FALSE_{iii}$ is independently performed for each feature quantity type as described above.

Figure 8:
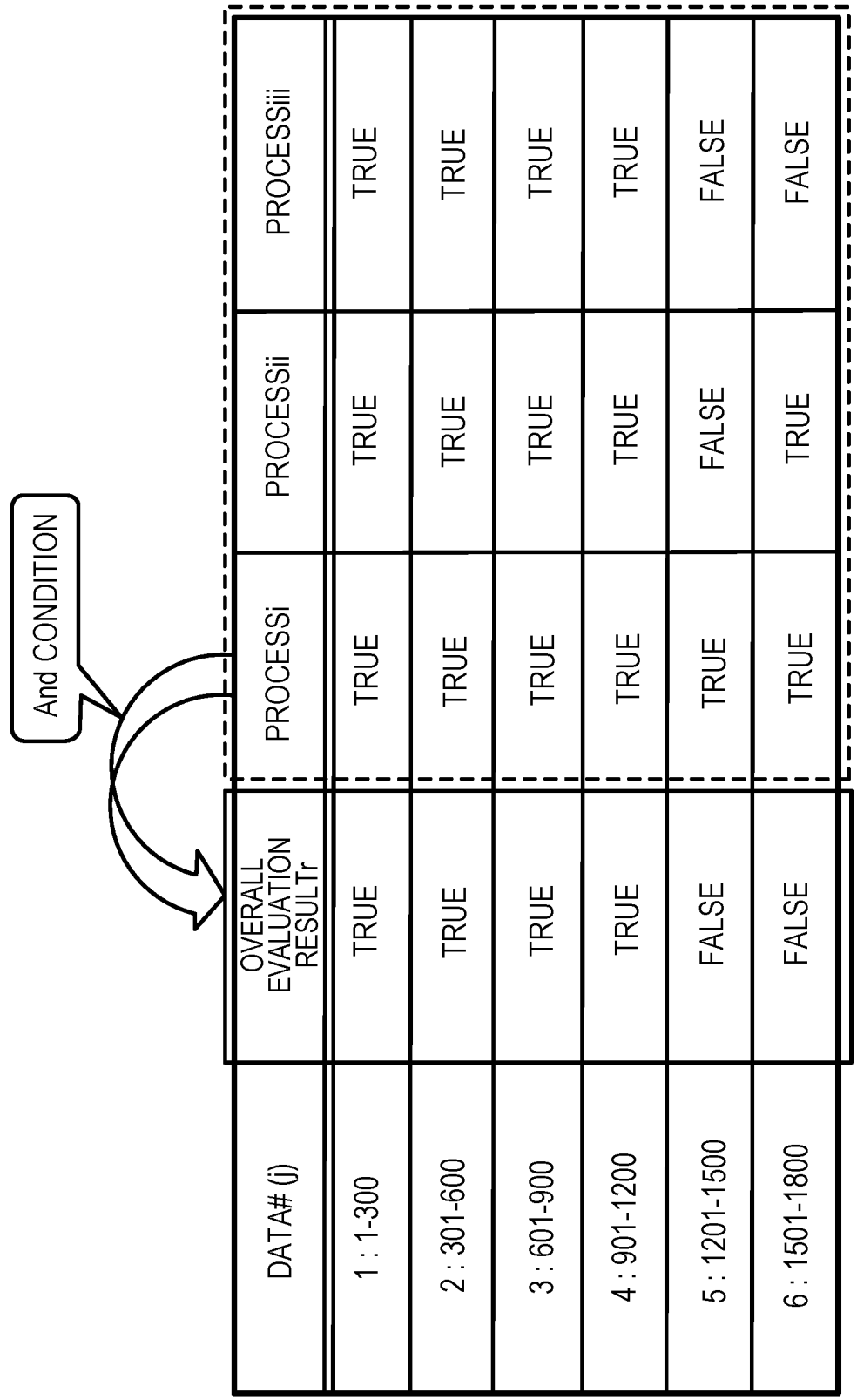
FIG. 8 is a diagram showing a relationship between each evaluation result and an overall evaluation result in the form of a table.

Next, overall evaluation after evaluation results are assigned to all divided ECGs with respect to various feature quantities through the processes i, ii and iii corresponding to S4f, S4e and S4h will be described. FIG. 8 is a diagram showing a relationship between each evaluation result and an overall evaluation result in the form of a table.

As shown in FIG. 8, a case in which overall evaluation is determined according to whether each evaluation result in the process i, ii and iii with respect to feature quantities calculated from the same data satisfies "And" condition is described. This overall evaluation is independently performed for each feature quantity type.

Each row pertaining to the column of Data #(j) shown in FIG. 8 represents a row corresponding to a j-th, here, first to sixth to-be-evaluated divided ECGs. For example, the row pertaining to "1:1-300" represents a row corresponding to data about the first to-be-evaluated divided ECG. In addition, "1-300" in "1:1-300" represents that ECG sampling numbers in the first to-be-evaluated divided ECG are 1 to 300, for example.

In addition, in FIG. 8, a TRUE evaluation result or a FALSE evaluation result is represented such that it corresponds to each row of the column of Data #(j) in (1) an overall evaluation result r item representing an overall evaluation result r, (2) a process i item representing an evaluation result of the process i, (3) a process ii item representing an evaluation result of the process ii, and (4) a process iii item representing an evaluation result of the process iii.

For example, the row pertaining to "2:301-600" shown in FIG. 8 represents a row corresponding to data about the second to-be-evaluated divided ECG, and represents that the TRUE evaluation result is assigned to all of the process i item, the process ii item and the process iii item corresponding to this row.

Accordingly, "And" condition is satisfied, and thus the overall evaluation result r item corresponding to the row of "2:301-600" represents the TRUE evaluation result.

Further, for example, the row of "5:1201-1500" shown in FIG. 8 represents a row pertaining to data about the fifth to-be-evaluated divided ECG, the process i item corresponding to this row represents the TRUE evaluation result, and the process ii item and the process iii item represent the FALSE evaluation result.

Accordingly, "And" condition is not satisfied, and thus the overall evaluation result r item corresponding to the row of "5:1201-1500" represents the FALSE evaluation result.

That is, when evaluation results with respect to one or more items among the process i, ii and iii items are FALSE for a certain type of feature quantity in a certain to-be-evaluated divided ECG, the evaluator 131e of the ECG measurement state evaluator 131 overall evaluates that measurement abnormalities have been generated in the to-be-evaluated divided ECG pertaining to the corresponding type of feature quantity and assigns $FALSE_{feature}$ quantity name to this ECG.

After overall evaluation results are assigned to all of the feature quantities a, b and c in S4f, S4e and S4h for the to-be-evaluated divided ECG, the evaluator 131e performs final evaluation of the to-be-evaluated divided ECG (S4j).

For example, when overall evaluation results with respect to one or more feature quantities among overall evaluation results of various feature quantities a, b and c of a certain to-be-evaluated divided ECG are FALSE, the evaluator 131e finally evaluates the to-be-evaluated divided ECG as an ECG having measurement abnormalities.

On the other hand, when all overall evaluation results of the feature quantities a, b and c of a certain to-be-evaluated divided ECG are TRUE, the evaluator 131e of the ECG measurement state evaluator 131 finally evaluates the to-be-evaluated divided ECG as a normal ECG.

Furthermore, when evaluation results with respect to all the processes i, ii and iii are not measurement abnormalities with respect to various feature quantities in a certain to-be-evaluated divided ECG, that is, when all evaluation results of the processes i, ii and iii corresponding to S4f, S4e and S4h are TRUE, the evaluator 131e of the ECG measurement state evaluator 131 finally evaluates the to-be-evaluated divided ECG as a normal ECG.

According to this evaluation, the evaluator 131e replaces this ECG with data about a temporally oldest ECG from among feature quantities stored in the ECG recorder 131f as a correct answer value that is temporally newest data. This data is used to be referred to in the aforementioned process iii.

When an evaluation result is FALSE in S4f, S4g, S4h or S4i with respect to a certain to-be-evaluated divided ECG, the evaluator 131e of the ECG measurement state evaluator 131 evaluates the to-be-evaluated divided ECG on the basis of the following expression (2) until TRUE that is an evaluation result with respect to a divided ECG that is an evaluation target after the current to-be-evaluated divided ECG is acquired instead of S4f, S4e and S4h.

$$\text{Statistics}_{target} \leq \mu_{ref} + w \times k \times \sigma_{ref} \quad \text{Expression (2)}$$

When deviation of an electrode occurs and the electrode is fixed again in a different place, that is, when a biosignal can be stably acquired at a potential different from an initial potential, there are cases in which a biosignal cannot be normally acquired at the same potential as that before deviation of the electrode.

Accordingly, it is possible to return to a state in which a biosignal can be normally acquired by using the expression (2) in which the coefficient k representing the weight of the standard deviation of the second term of the right side of the aforementioned expression (1) is multiplied by w.

By using the expression (2), a range regarded as normal values is extended and thus a condition for evaluating whether it is a state in which a biosignal can be normally acquired can be mitigated. Accordingly, it is also possible to curb omission of detection of returning from a state that is a measurement abnormality.

The instantaneous heartbeat evaluator 125 evaluates the instantaneous heartbeat on the basis of the evaluation result obtained by the ECG measurement state evaluator 131 in S4 (S5). Meanwhile, although the aforementioned conventional method c may be executed in combination with the process of S5, in such a case, instantaneous heartbeat measurement state evaluation based on potential amplitude characteristics of R waves, described in the aforementioned conventional method c, is performed prior to the process of S5.

In the present embodiment, a case in which values represented by only evaluation results obtained by the aforementioned ECG measurement state evaluator 131 is described. When two types of measurement states of a normal measurement state and artifacts are considered as an example of a measurement state of R waves, the instantaneous heartbeat evaluator 125 regards all R waves detected in divided ECGs identified as measurement abnormalities by the ECG measurement state evaluator 131 as measurement abnormalities and regards the R waves as artifacts.

In addition, the instantaneous heartbeat evaluator 125 regards all R waves detected in divided ECGs identified as normal by the ECG measurement state evaluator 131 as normal.

The instantaneous heartbeat evaluator 125 evaluates a measurement state of an instantaneous heartbeat composed of two R waves neighboring in a time series on the basis of a measurement state identified with respect to each R wave. When two types of measurement states of a normal measurement state and artifacts are considered, a combination of identification results of measurement states of R waves constituting an instantaneous heartbeat is any of patterns represented by serial numbers #1, #2, #3 and #4 shown in the following table 1. Meanwhile, the form of the serial numbers is not limited to the aforementioned one.

TABLE 1

| # | Determination result | Details of state | Evaluation value |
|---|---|---|---|
| 1 | "R", "R" | Both are normal measurement states | 1 |
| 2 | "R", "A" | One side is a normal measurement state and the other is artifacts | 0.4 |
| 3 | "A", "R" | | |
| 4 | "A", "A" | Both are artifacts | 0 |

In Table 1, an identification result "R" represents a normal measurement state and "A" represents artifacts. That is, an identification result "R, R" corresponding to serial number #1 in Table 1 represents that both measurement state identification results of first and second R waves neighboring in a time series are normal measurement states.

An identification result "R, A" corresponding to serial number #2 in Table 1 represents that a measurement state identification result of the first R wave between two R waves neighboring in the time series is a normal state and a measurement state identification result of the second R wave is artifacts. An identification result "A, R" corresponding to serial number #3 in Table 1 represents that a measurement state identification result of the first R wave between two R waves neighboring in the time series is artifacts and a measurement state identification result of the second R wave is a normal state.

An identification result "A, A" corresponding to serial number #4 in Table 1 represents that both measurement state identification results of the first and second R waves neighboring in the time series are artifacts.

"Details of state" in Table 1 represents details of measurement states of the two R waves neighboring in the time series based on an identification result of the same row in Table 1.

Only a combination of identification results of measurement states of two R waves constituting an instantaneous heartbeat is distinguished by representation of "details of state" and states before and after the time series are not distinguished thereby.

That is, although there are four combinations of measurement state identification results corresponding to serial numbers #1, #2, #3 and #4 in the example shown in Table 1, "details of state" corresponding to #2 and #3 are the same "one side is a normal measurement state and the other is artifacts". Accordingly, there are three "details of state" in Table 1.

Although a case in which evaluation is performed for each "details of state" of Table 1 is described in the present embodiment, other evaluation standards may be set. For example, an evaluation standard by which information before and after two R waves neighboring in the time series can be identified even for the same "details of state" may be set.

The instantaneous heartbeat evaluator 125 allocates separate evaluation values to respective states such that a user can easily distinguish details of states. An example of an evaluation value is represented as "evaluation value" in Table 1. Meanwhile, this evaluation value is merely an example and a method of determining an evaluation value is not particularly limited in the present embodiment.

Next, "evaluation value" in Table 1 will be described. This "evaluation value" represents the reliability of a measurement state of each of two R waves constituting an instantaneous heartbeat and neighboring in the time series, which is a state represented by "details of state" of the same row in Table 1, using a numerical value between 0 to 1, and an arbitrary evaluation value is allocated to each state represented by "details of state".

Meanwhile, the range of evaluation values and an evaluation value pitch for each state are not particularly limited, and different evaluation values with a pitch of 1 may be allocated to respective states between 1 to 10 or evaluation values for states may have different pitch widths, for example.

Furthermore, lengths of a horizontal bar graph (for example, reliability is higher when a length of the horizontal bar graph is longer) and the like may be used instead of evaluation values.

A specific example of evaluation values will be described. As shown in Table 1, when "details of state" corresponding to the serial number #1 is "both are normal measurement states", "evaluation value" corresponding to this serial number #1 is "1" that is a maximum value.

Furthermore, only a combination of identification results of measurement states of two R waves constituting an instantaneous heartbeat is distinguished by representation of "evaluation value" and states before and after the time series are not distinguished like the representation of "details of state".

That is, "details of state" corresponding to the serial numbers #2 and #3 are commonly "one side is a normal measurement state and the other is artifacts" and "evaluation value" corresponding to these serial numbers #2 and #3 is commonly "0.4" obtained by subtracting 0.6 from "evaluation value" corresponding to the serial number #1.

"Details of state" corresponding to the serial number #4 is "both are artifacts" and "evaluation value" corresponding to this serial number #4 is "0" that is a minimum value reduced by 0.4 from "evaluation value" in #2 and #3.

The instantaneous heartbeat abnormal value processor 132 regards instantaneous heartbeats with values lower than an evaluation value set for abnormal value identification as abnormal values on the basis of an evaluation result obtained by the instantaneous heartbeat evaluator 125 and excludes the instantaneous heartbeats from instantaneous heartbeats to be transferred to subsequent processing (36).

When artifacts are not included in instantaneous heartbeats to be transferred to subsequent processing, for example, in the case of calculation of heart rate feature quantities, or the like, the aforementioned evaluation value "1" is necessary and thus the instantaneous heartbeat abnormal value processor 132 regards instantaneous heartbeats having evaluation values less than this evaluation value as abnormal values and excludes these instantaneous heartbeats from instantaneous heartbeats to be transferred to subsequent processing.

The overview of the present embodiment has been described above. Although set values i, j and k used for evaluation in the aforementioned processes i, ii and iii are not specified in detail in the present embodiment, it is conceivable to use divided ECGs corresponding to j=2, that is, divided ECGs before and after a to-be-evaluated divided ECG for the process ii, for example.

Here, it is possible to detect long-term measurement abnormalities that are difficult to completely detect only with the process ii by setting the number of divided ECGs used for evaluation in the processes i and iii to j<i, k.

With respect to overall evaluation in the aforementioned S4i and final evaluation in S4j, the evaluator 131e may set presence or absence of one or more FALSE evaluations as a criterion for assigning TRUE or FALSE and assign TRUE or FALSE to a certain to-be-evaluated divided ECG as in the above-described S4f, S4g and S4h. That is, it is possible to assign TRUE or FALSE to a certain to-be-evaluated divided ECG in overall evaluation and final evaluation on the basis of the number of evaluations assigned with FALSE in the above-described S4f, S4g and S4h instead of performing evaluation in AND condition of TRUE.

In addition, although a case in which only artifacts that are difficult to identify as R waves using frequency characteristics and amplitude characteristics are regarded as targets to be excluded as abnormal values of instantaneous heartbeats has been described in the present embodiment, low-frequency baseline fluctuations may be included in ECG measurement abnormalities and these may be included in targets to be excluded as abnormal values of instantaneous heartbeats.

In such a case, the ECG measurement state evaluator 131 may skip noise removal performed in S4a and perform S4b immediately after S3.

Furthermore, the above-described measurement abnormality identification is not limited to ECG, and measurement abnormality identification may be performed on signals of a circulatory system which have the same features as those of ECG, such as pulse waves.

When measurement abnormality identification is performed on pulse waves, it is desirable to use a waveform having a maximum value corresponding to a P wave of pulse waves (a waveform having a maximum value corresponding to depolarization of the heart) instead of the R wave used for ECG.

Next, effects obtained by an embodiment of the present invention will be described.

In an embodiment of the present invention, the influence of artifacts that are difficult to identify only using frequency characteristics and potential amplitude characteristics on heart rate variability analysis is reduced by evaluating ECG measurement states in advance and executing abnormal values of instantaneous heartbeats using the evaluation result.

In addition, in an embodiment of the present invention, both a waiting time taken to identify ECG measurement states and the influence of measurement states of referred divided ECGs on evaluation are reduced by referring to a plurality of types of divided ECGs in response to an evaluation method in ECG measurement state evaluation and then performing final evaluation using statistics of the evaluation result.

Meanwhile, the present invention is not limited to the above-described embodiment and various modifications and applications can be made without departing from the spirit and scope of the present invention. In addition, embodiments may be appropriately combined to be implemented, and such a case, combined effects are obtained. Furthermore, the above-described embodiment includes inventions of various stages and various inventions can be derived by appropriately combining a plurality of disclosed components.

Moreover, a method described in each embodiment can be stored in a recording medium such as magnetic disk (a floppy (registered trademark) disk, a hard disk, or the like), an optical disk (a CD-ROM, a DVD, an MO, or the like), or a semiconductor memory (a ROM, a RAM, a flash memory, or the like), for example, as a program (software means) executable by a calculator (computer) and also can be transmitted and distributed through a communication medium. Meanwhile, programs stored in a medium also include a setting program for configuring a software means (including tables and a data structure as well as an execution program) executed by a calculator in the calculator. A calculator which realizes the present apparatus executes the above-described processes by reading a program recorded in a recording medium, constructing software means according to the setting program according to circumstances, and performing operation control according to the software means. Further, a recording medium mentioned in the present specification is not limited to a recording medium for distribution and includes a storage medium such as a magnetic disk and a semiconductor memory provided in a calculator or an apparatus connected via a network.

REFERENCE SIGNS LIST

10 Instantaneous heartbeat reliability evaluation apparatus
11 ECG measurement unit
12 Instantaneous heartbeat reliability evaluation unit
121 R-wave extractor
122 R-wave related information recorder
123 Instantaneous heartbeat calculator
124 Instantaneous heartbeat recorder
125 Instantaneous heartbeat evaluator
131 ECG measurement state evaluator
132 Instantaneous heartbeat abnormal value processor

The invention claimed is:

1. An instantaneous heartbeat reliability evaluation apparatus comprising:
   extraction means which extracts waveforms having a maximum value corresponding to depolarization of a heart in a biosignal of an examinee on a basis of a signal output from measurement means for measuring the biosignal of the examinee;
   first calculation means which calculates an interval between two of the waveforms neighboring in a time series and extracted by the extraction means;
   dividing means which divides a signal output from the measurement means into signals of predetermined periods;
   second calculation means which calculates feature quantities of a potential of each signal divided by the dividing means, wherein the feature quantities comprise: at least one of
      a first feature quantity representing a magnitude of a potential of each of the divided signals for the signals divided by the dividing means,
      a second feature quantity representing variation in the potential of each of the divided signals for the signals divided by the dividing means, and
      a third feature quantity representing change in a time series in the potential of each of the divided signals for the signals divided by the dividing means;
   first evaluation means which evaluates, on the basis of the feature quantities calculated by the second calculation means with respect to a signal of an evaluation target that is one of the signals divided by the dividing means, and the feature quantities calculated by the second calculation means with respect to another signal belonging to a set of signals successive in a time series including the signal of the evaluation target, whether a measurement state of the signal of the evaluation target is likely to be normal or likely to be abnormal for each of types of the feature quantities calculated by the second calculation means, and evaluates whether a measurement state of each signal divided by the dividing means is normal or abnormal on a basis of the feature quantities calculated by the second calculation means; and
   second evaluation means which evaluates measurement states of the two neighboring waveforms extracted by the extraction means on a basis of an evaluation result obtained by the first evaluation means and evaluates reliability of a measurement state of the interval between the waveforms calculated by the first calculation means depending on a type of the evaluated measurement states of the waveforms.

2. The instantaneous heartbeat reliability evaluation apparatus according to claim 1, wherein the first evaluation means evaluates, on the basis of feature quantities calculated by the second calculation means with respect to a signal of an evaluation target that is one of the signals divided by the dividing means, and feature quantities calculated by the second calculation means with respect to a signal neighboring the signal of the evaluation target in a time series, whether a measurement state of the signal of the evaluation target is likely to be normal or likely to be abnormal for each of types of the feature quantities calculated by the second calculation means, and evaluates whether measurement states of the signals divided by the dividing means are normal or abnormal on the basis of an evaluation result for each feature quantity type.

3. The instantaneous heartbeat reliability evaluation apparatus according to claim 1, wherein
   the first evaluation means evaluates, on the basis of feature quantities calculated by the second calculation means with respect to a signal of an evaluation target that is one of the signals divided by the dividing means, and feature quantities calculated by the second calculation means with respect to a signal for which a measurement state has been evaluated as normal in advance among the signals divided by the dividing means, whether a measurement state of the signal of the evaluation target is likely to be normal or likely to be abnormal for each of types of the feature quantities calculated by the second calculation means, and evaluates whether measurement states of the signals divided by the dividing means are normal or abnormal on the basis of an evaluation result for each feature quantity type.

4. The instantaneous heartbeat reliability evaluation apparatus according to claim 1, wherein the first evaluation means
   acquires, on the basis of feature quantities calculated by the second calculation means with respect to a signal of an evaluation target that is one of the signals divided by the dividing means, and feature quantities calculated by the second calculation means with respect to another signal belonging to a set of signals successive in a time series including the signal of the evaluation target, a first evaluation result representing whether a measurement state of the signal of the evaluation target is likely to be normal or likely to be abnormal for each of types of the feature quantities calculated by the second calculation means,
   acquires a second evaluation result representing whether a measurement state of the signal of the evaluation target is likely to be normal or likely to be abnormal for each of types of the feature quantities calculated by the second calculation means on the basis of feature quantities calculated by the second calculation means with respect to the signal of the evaluation target that is one of the signals divided by the dividing means, and feature quantities calculated by the second calculation means with respect to a signal neighboring the signal of the evaluation target in a time series, acquires a third evaluation result representing whether a measurement state of the signal of the evaluation target is likely to be normal or likely to be abnormal for each of types of the feature quantities calculated by the second calculation means on the basis of feature quantities calculated by the second calculation means with respect to the signal of the evaluation target, and feature quantities calculated by the second calculation means with respect to a signal for which a measurement state has been evaluated as normal in advance, and evaluates the measurement state of the signal of the evaluation target as abnormal when at least one of the first, second and third evaluation results represents that the measurement state of the signal of the evaluation target is likely to be abnormal.

5. The instantaneous heartbeat reliability evaluation apparatus according to claim 1, wherein the second evaluation means evaluates the measurement states of the waveforms extracted by the extraction means as abnormal from a signal for which a measurement state has been evaluated as abnormal by the first evaluation means, and evaluates the measurement states of the waveforms extracted by the extraction means as normal from a signal for which a measurement state has been evaluated as normal by the first evaluation means.

6. An instantaneous heartbeat reliability evaluation method performed by an instantaneous heartbeat reliability evaluation apparatus, comprising:
    extracting waveforms having a maximum value corresponding to depolarization of a heart in a biosignal of an examinee;
    calculating an interval between two of the extracted waveforms neighboring in a time series;
    dividing the biosignal into signals of predetermined periods;
    calculating feature quantities of a potential of each of the divided signals, wherein the feature quantities comprise: at least one of
        a first feature quantity representing a magnitude of a potential of each of the divided signals,
        a second feature quantity representing variation in the potential of each of the divided signals, and
        a third feature quantity representing change in a time series in the potential of each of the divided signals;
    evaluating, on the basis of the calculated feature quantities with respect to a signal of an evaluation target that is one of the divided signals, and the calculated feature quantities with respect to another signal belonging to a set of signals successive in a time series including the signal of the evaluation target, whether a measurement state of the signal of the evaluation target is likely to be normal or likely to be abnormal for each of types of the calculated feature quantities;
    evaluating whether a measurement state of each of the divided signals is normal or abnormal on a basis of the calculated feature quantities;
    evaluating measurement states of the two neighboring extracted waveforms on a basis of an evaluation result of a measurement state of each of the divided signals; and
    evaluating reliability of a measurement state of the calculated interval between the waveforms depending on a type of the evaluated measurement states of the waveforms.

7. The instantaneous heartbeat reliability evaluation method according to claim 6, further comprising:
    evaluating, on the basis of feature quantities calculated with respect to a signal of an evaluation target that is one of the signals divided, and feature quantities calculated with respect to a signal neighboring the signal of the evaluation target in a time series, whether a measurement state of the signal of the evaluation target is likely to be normal or likely to be abnormal for each of types of the feature quantities calculated, and
    evaluating whether measurement states of the signals divided are normal or abnormal on the basis of an evaluation result for each feature quantity type.

8. The instantaneous heartbeat reliability evaluation method according to claim 6, further comprising:
    evaluating, on the basis of feature quantities calculated with respect to a signal of an evaluation target that is one of the signals divided, and feature quantities calculated with respect to a signal for which a measurement state has been evaluated as normal in advance among the signals divided, whether a measurement state of the signal of the evaluation target is likely to be normal or likely to be abnormal for each of types of the feature quantities calculated, and
    evaluating whether measurement states of the signals divided are normal or abnormal on the basis of an evaluation result for each feature quantity type.

9. The instantaneous heartbeat reliability evaluation method according to claim 6, further comprising:
    acquiring, on the basis of feature quantities calculated with respect to a signal of an evaluation target that is one of the signals divided, and feature quantities calculated with respect to another signal belonging to a set of signals successive in a time series including the signal of the evaluation target, a first evaluation result representing whether a measurement state of the signal of the evaluation target is likely to be normal or likely to be abnormal for each of types of the feature quantities calculated,
    acquiring a second evaluation result representing whether a measurement state of the signal of the evaluation target is likely to be normal or likely to be abnormal for each of types of the feature quantities calculated on the basis of feature quantities calculated with respect to the signal of the evaluation target that is one of the signals divided, and feature quantities calculated with respect to a signal neighboring the signal of the evaluation target in a time series,
    acquiring a third evaluation result representing whether a measurement state of the signal of the evaluation target is likely to be normal or likely to be abnormal for each of types of the feature quantities calculated on the basis of feature quantities calculated with respect to the signal of the evaluation target, and feature quantities calculated with respect to a signal for which a measurement state has been evaluated as normal in advance, and
    evaluating the measurement state of the signal of the evaluation target as abnormal when at least one of the first, second and third evaluation results represents that the measurement state of the signal of the evaluation target is likely to be abnormal.

10. The instantaneous heartbeat reliability evaluation method according to claim 6, further comprising:
  evaluating the measurement states of the waveforms extracted as abnormal from a signal for which a measurement state has been evaluated as abnormal, and
  evaluating the measurement states of the waveforms extracted as normal from a signal for which a measurement state has been evaluated as normal.

11. A non-transitory computer readable medium storing one or more instructions causing a processor to execute:
  extracting waveforms having a maximum value corresponding to depolarization of a heart in a biosignal of an examinee;
  calculating an interval between two of the extracted waveforms neighboring in a time series;
  dividing the biosignal into signals of predetermined periods;
  calculating feature quantities of a potential of each of the divided signals, wherein the feature quantities comprise: at least one of
    a first feature quantity representing a magnitude of a potential of each of the divided signals,
    a second feature quantity representing variation in the potential of each of the divided signals, and
    a third feature quantity representing change in a time series in the potential of each of the divided signals;
  evaluating, on the basis of the calculated feature quantities with respect to a signal of an evaluation target that is one of the divided signals, and the calculated feature quantities with respect to another signal belonging to a set of signals successive in a time series including the signal of the evaluation target, whether a measurement state of the signal of the evaluation target is likely to be normal or likely to be abnormal for each of types of the calculated feature quantities;
  evaluating whether a measurement state of each of the divided signals is normal or abnormal on a basis of the calculated feature quantities;
  evaluating measurement states of the two neighboring extracted waveforms on a basis of an evaluation result of a measurement state of each of the divided signals; and
  evaluating reliability of a measurement state of the calculated interval between the waveforms depending on a type of the evaluated measurement states of the waveforms.

12. The non-transitory computer readable medium according to claim 11, wherein the one or more instructions causing a processor to further execute:
  evaluating, on the basis of feature quantities calculated with respect to a signal of an evaluation target that is one of the signals divided, and feature quantities calculated with respect to a signal neighboring the signal of the evaluation target in a time series, whether a measurement state of the signal of the evaluation target is likely to be normal or likely to be abnormal for each of types of the feature quantities calculated, and
  evaluating whether measurement states of the signals divided are normal or abnormal on the basis of an evaluation result for each feature quantity type.

13. The non-transitory computer readable medium according to claim 11, wherein the one or more instructions causing a processor to further execute:
  evaluating, on the basis of feature quantities calculated with respect to a signal of an evaluation target that is one of the signals divided, and feature quantities calculated with respect to a signal for which a measurement state has been evaluated as normal in advance among the signals divided, whether a measurement state of the signal of the evaluation target is likely to be normal or likely to be abnormal for each of types of the feature quantities calculated, and
  evaluating whether measurement states of the signals divided are normal or abnormal on the basis of an evaluation result for each feature quantity type.

14. The non-transitory computer readable medium according to claim 11, wherein the one or more instructions causing a processor to further execute:
  acquiring, on the basis of feature quantities calculated with respect to a signal of an evaluation target that is one of the signals divided, and feature quantities calculated with respect to another signal belonging to a set of signals successive in a time series including the signal of the evaluation target, a first evaluation result representing whether a measurement state of the signal of the evaluation target is likely to be normal or likely to be abnormal for each of types of the feature quantities calculated,
  acquiring a second evaluation result representing whether a measurement state of the signal of the evaluation target is likely to be normal or likely to be abnormal for each of types of the feature quantities calculated on the basis of feature quantities calculated with respect to the signal of the evaluation target that is one of the signals divided, and feature quantities calculated with respect to a signal neighboring the signal of the evaluation target in a time series,
  acquiring a third evaluation result representing whether a measurement state of the signal of the evaluation target is likely to be normal or likely to be abnormal for each of types of the feature quantities calculated on the basis of feature quantities calculated with respect to the signal of the evaluation target, and feature quantities calculated with respect to a signal for which a measurement state has been evaluated as normal in advance, and
  evaluating the measurement state of the signal of the evaluation target as abnormal when at least one of the first, second and third evaluation results represents that the measurement state of the signal of the evaluation target is likely to be abnormal.

15. The non-transitory computer readable medium according to claim 11, wherein the one or more instructions causing a processor to further execute:
  evaluating the measurement states of the waveforms extracted as abnormal from a signal for which a measurement state has been evaluated as abnormal, and
  evaluating the measurement states of the waveforms extracted as normal from a signal for which a measurement state has been evaluated as normal.

* * * * *